(12) United States Patent
Bluecher et al.

(10) Patent No.: US 11,298,440 B2
(45) Date of Patent: *Apr. 12, 2022

(54) MICROSTRUCTURED HAPTOTAXIC IMPLANT

(71) Applicant: BVW Holding AG, Cham (CH)

(72) Inventors: Lukas Bluecher, Eurasberg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/236,738

(22) Filed: Apr. 21, 2021

(65) Prior Publication Data

US 2021/0290820 A1 Sep. 23, 2021

Related U.S. Application Data

(63) Continuation of application No. 15/809,766, filed on Nov. 10, 2017, now Pat. No. 11,013,827, which is a
(Continued)

(51) Int. Cl.
*A61L 27/26* (2006.01)
*A61L 27/56* (2006.01)
(Continued)

(52) U.S. Cl.
CPC ............ *A61L 27/26* (2013.01); *A61F 2/0077* (2013.01); *A61L 27/48* (2013.01); *A61L 27/50* (2013.01);
(Continued)

(58) Field of Classification Search
CPC .......... A61L 27/26; A61L 27/48; A61L 27/50; A61L 27/56; A61L 27/58; A61L 2400/12;
(Continued)

(56) References Cited

U.S. PATENT DOCUMENTS 9,120,670 B2 9/2015 Hulseman et al.
9,908,274 B2 3/2018 Hulseman et al.
(Continued)

FOREIGN PATENT DOCUMENTS

CN 101035574 A 9/2007
CN 103919629 A 7/2014
(Continued)

OTHER PUBLICATIONS

Li et al., "Fabrication of patterned multi-walled poly-l-lactic acid conduits for nerve regeneration", Journal of Neuroscience Methods, 165 (2):257-264, Aug. 10, 2007.
(Continued)

*Primary Examiner* — Brian A Dukert
*Assistant Examiner* — Rebecca Lynee Zimmerman
(74) *Attorney, Agent, or Firm* — Patterson Intellectual Property Law, P.C.; Ryan D. Levy; Mark A. Kilgore

(57) ABSTRACT

The invention relates to the field of tissue engineering and regenerative medicine, and particularly to a three-dimensional biomimetic tissue scaffold that exploits the use of three-dimensional print technology. Surface energy is controlled by precisely placing polymers with differing surface chemistry, and using surface texture and bulk composition to pattern absorbable and non-absorbable polymers for the purpose of promoting functional healing in a mammalian body.

20 Claims, 11 Drawing Sheets

Related U.S. Application Data continuation of application No. PCT/US2017/003046, filed on May 1, 2017.

(60) Provisional application No. 62/330,104, filed on Apr. 30, 2016.

(51) Int. Cl.
  *A61L 27/58* (2006.01)
  *A61F 2/00* (2006.01)
  *A61L 27/48* (2006.01)
  *A61L 27/50* (2006.01)

(52) U.S. Cl.
  CPC .............. *A61L 27/56* (2013.01); *A61L 27/58* (2013.01); *A61F 2/0063* (2013.01); *A61F 2002/0081* (2013.01); *A61F 2002/0086* (2013.01); *A61F 2250/0031* (2013.01); *A61F 2250/0056* (2013.01); *A61L 2400/12* (2013.01)

(58) Field of Classification Search
  CPC ............ A61F 2/0077; A61F 2002/0086; A61F 2/0063; A61F 2250/0031; A61F 2002/0081; A61F 2250/0056; A61F 2/0059; A61F 2210/0076; A61F 2002/0068; A61F 2/2481
  See application file for complete search history.

(56) References Cited

U.S. PATENT DOCUMENTS

| | | |
|---|---|---|
| 9,988,201 B2 | 6/2018 | Darin et al. |
| 10,377,044 B2 | 8/2019 | Hulseman et al. |
| 10,458,053 B2 | 10/2019 | Hulseman et al. |
| 10,575,667 B2 | 3/2020 | Hulseman et al. |
| 10,687,642 B2 | 6/2020 | Hulseman et al. |
| 10,889,005 B2 | 1/2021 | Hulseman et al. |
| 2005/0244455 A1* | 11/2005 | Greenawalt ........... A61F 2/0063 424/423 |
| 2008/0112998 A1 | 5/2008 | Wang |
| 2010/0151114 A1* | 6/2010 | Parrott .................. D06M 10/08 427/2.26 |
| 2013/0103079 A1 | 4/2013 | Lau et al. |
| 2013/0150763 A1* | 6/2013 | Mirzaei ................ A61K 9/7007 602/43 |
| 2014/0249362 A1* | 9/2014 | Sheu .................... A61L 31/148 600/30 |
| 2015/0368838 A1 | 12/2015 | Hulseman et al. |
| 2017/0014111 A1 | 1/2017 | Hulseman et al. |
| 2019/0062155 A1 | 2/2019 | Hulseman et al. |
| 2020/0338808 A1 | 10/2020 | Hulseman et al. |
| 2021/0086371 A1 | 3/2021 | Hulseman et al. |

FOREIGN PATENT DOCUMENTS

| | | |
|---|---|---|
| TW | 200925342 A | 6/2009 |
| WO | 9511007 | 4/1995 |
| WO | 2005105172 A1 | 11/2005 |
| WO | 2009049565 A | 4/2009 |

OTHER PUBLICATIONS

Lo Chun-Min et al., "Cell Movement Is Guided by the Rigidity of the Substrate", Biophysical Journal 79 (1):144-152, Jul. 2, 2000.

* cited by examiner

MICROSTRUCTURED HAPTOTAXIC IMPLANT

CROSS-REFERENCE TO RELATED APPLICATIONS

This application is a continuation of U.S. patent application Ser. No. 15/809,766 filed Nov. 10, 2017, which claims benefit of priority to U.S. Provisional Application No. 62/330,104, filed on Apr. 30, 2016, the contents of which are hereby incorporated by reference in their entirety.

TECHNICAL FIELD

The present disclosure provides in part engineered biomaterials, including a patterned biomaterial having organized fibers or drops capable of acting as a synthetic extracellular matrix for promoting wound repair.

BACKGROUND OF THE INVENTION

The stiffness and elasticity of extracellular matrix in living tissue has important implications in cell migration, gene expression, and differentiation. More precisely, microscopic variations in stiffness and elasticity appear to be an important differentiating property of natural and synthetic tissue scaffolds. Cells actively sense extracellular matrix rigidity and migrate preferentially towards stiffer surfaces in a phenomenon called durotaxis. They also detect elasticity and adjust their gene expression accordingly which has increasingly become a subject of research because of its impact on differentiation and functional wound healing.

Lo and colleagues formulated the hypothesis that individual cells can detect substrate stiffness by a process of active tactile exploration in which cells exert contractile forces and measure the resulting deformation in the substrate.

We have discovered that surface energy or hydrophobicity, or more precisely the microscopic variation of surface energy, is the underlying driver of durotaxis. High stiffness and low elasticity is correlated with high surface energy at microscopic scale. The elasticity sensed by cells is a combination of the Young's modulus of the substrate and the rigidity of the cellular attachment. Since the tensile strength of the cellular attachment is strongly affected by the surface energy of the substrate, we have found that surface energy is important in cell motility and functionality. The stiffness of the substrate is important in the equilibrium achieved by the factors of 1) deformation of the substrate, 2) strength of cell attachment, and 3) the resulting deformation of the cell shape due to factors (1) and (2).

In the body, microscopic differences in rigidity and hydrophobicity within the extracellular matrix is a result of the qualitative and quantitative biochemical properties of the extracellular matrix. In particular, the concentration, distribution and categories of the various macromolecules that form the extracellular matrix meshwork. Though the extracellular matrix is composed of many intracellularly-synthesized components—including a number of glycosaminoglycans and fibrous proteins such as fibronectin, laminin, collagen, and elastin—it is the latter two fibrous proteins that are most influential in defining the mechanical properties of natural extracellular matrix.

The mechanical behavior of materials at the microscopic scale is often different from that at macroscopic scale. At the microscopic scale surface effects may control the deformation properties due to the increasing surface to volume ratio where surface effects become predominant and can significantly modify the macroscopic properties of cellular dynamics.

Both elastin and collagen are proteins rich in hydrophobic amino acids such as glycine and proline, which form mobile hydrophobic regions bounded by crosslinks between lysine residues. Differences in the hydrophobicity of collagen compared to elastin contributes to elastin being the elastic element in extracellular matrix and collagen being the stiffening element in extracellular matrix.

These two constituents exist in alternating fashion in extracellular matrix. These observations have lead to the present novel disclosure of a synthetic extracellular matrix mimic or patterned biomaterial that is structurally and functionally different from existing synthetic tissue scaffolds and soft tissue mesh. These novelty and utility of the present patterned biomaterial will be understood more completely in view of the following background material.

Cell adhesion is the binding of a cell to a surface or substrate, such as extracellular matrix. Adhesion occurs from the action of proteins, called cell adhesion molecules, or sometimes adhesins. Examples of these proteins include selectins, integrins, and cadherins. The action of these proteins is highly controlled by the surface energy or hydrophobicity of a surface. Cellular adhesion is essential in cell motility and wound healing.

Adhesion occurs by reversible reactions which occur on cell surface proteins which are triggered by variations in surface energy. Forces and interactions may include hydrolysis/hydrophobic reactions, electrostatic reactions, Brownian motion, and facilitation by polysaccharides or biofilm polymers.

We have surprisingly found that the spatial frequency of adjacent surfaces is important in facilitating lamellipodia attachment, cellular polarization, and ultimately cellular motility. This finding is consistent with the structure of extracellular matrix.

The animal extracellular matrix includes the interstitial matrix which is hydrophilic relative to the basement membrane. Interstitial matrix is present between various animal cells in the intercellular spaces. Gels of polysaccharides and fibrous proteins fill the interstitial space and act as an orienting environment relative to the basement membrane. Basement membranes are sheet-like depositions of hyaluronic acid on which various epithelial cells rest. Hyaluronic acid (Hyaluronan) is a polysaccharide consisting of alternating residues on D-glucuronic acid and N-acetyl-glucosamine, which also differ in their hydrophilicity. Hyaluronic acid in bulk is relatively hydrophobic and does not readily dissolve in water. It is not found as a hydrophilic proteoglycan. Hyaluronan is a polymer of disaccharides, themselves composed of D-glucuronic acid and D-N-acetyl-glucosamine, linked via glycosidic bonds. Hyaluronan can be 25,000 disaccharide repeats in length.

On the other hand, proteoglycans have a net negative charge that attracts positively charged sodium ions, which attracts water molecules via osmosis, keeping the ECM and resident cells hydrated. Proteoglycans may also help to trap and store growth factors within the ECM. Thus, it can be seen on theoretical grounds that a hydrophobic polarizing structure surrounded by a hydrophilic environment, or more simply an alternating hydrophilic/hydrophobic structure (as represented by the molecular structure of Hyaluronan), is important in cell motility.

Haptotaxis is the directional motility or outgrowth of cells, usually up a gradient of high surface energy cellular adhesion sites or substrate-bound chemoattractants. Haptotaxis is distinguished from chemotaxis in that the chemoattraction is being expressed or bound on a surface, rather than the gradient in a fluid. In order for cells to migrate, the outer cell membrane needs to be directed or polarized, otherwise the cell membrane cannot develop a leading and trailing orientation.

We have discovered that alternating regions of hydrophobicity/hydrophilicity is important in haptotaxis. Further, one distinguishing feature between living extracellular matrix and synthetic tissue scaffolds is the presence of haptotaxis. Haptotaxic gradients are naturally present in the extracellular matrix of the body during processes such as angiogenesis. Researchers have attempted to mimic extracellular matrix by designing biomaterials where gradients are established by altering the concentration of adhesion sites on a polymer substrate. However, discretizing adhesion sites does not provide the polarization needed to promote cellular motility.

In wound repair, cells move through the extracellular matrix via lamellipodia. The lamellipodium is a cytoskeletal protein actin projection formed at a polarized edge of a cell. It contains a quasi-two-dimensional actin mesh; the whole structure propels the cell across a substrate. Lamellipodia are a characteristic feature at the front, leading edge, of motile cells. They are believed to be the actual motor which pulls the cell forward during the process of cell migration. The tip of the lamellipodium is the site where exocytosis occurs in migrating mammalian cells as part of their clathrin-mediated endocytic cycle. This, together with actin-polymerisation promoted by a high energy surface, helps extend the lamella forward and thus advance the cell's front. It thus acts as a steering device for cells.

Cell polarity arises primarily through the localization of specific proteins to specific areas of the cell membrane. Cell polarization affects cell shape and cell functions, including proliferation, differentiation, apoptosis, and motility [O'Neill et al., 1986; Singhvi et al., 1994; Chen et al., 1997; Baill et al., 1998; Dike et al., 1999]. For example, cells can be switched between growth and death programs by varying the size and spatial frequency of discretized attachment [Chen et al., 1997]. In general, total cellular mass increases as cell spreading is promoted, whereas apoptosis is observed in cells where cell spreading is discouraged. Based on the observation that cell growth is correlated more closely with the extent of cellular spreading than the total area of cellular adhesion, it seems likely cellular polarization is more important to cell motility than providing a featureless surface on which cells can attach and live.

Strategies for regenerating tissue usually involve promoting some aspect of cellular function, such as motility and differentiation. Unlike blood or bone marrow tissues which can be regenerated by intravenous injection of cells, regeneration of most tissues requires a template to guide their growth. Two-dimensional patterns are weak representations of the real cell environment and therefore there is great need to create structures or scaffolds that exhibit similar spatial control of bioactive molecules as those of 2D surfaces but within a 3D geometry. The extracellular matrix found in living tissues is a complex 3D highly hydrated environment made from many elements such as soluble or surface bound molecules, proteins, enzymes, and physical cues like pores and topographies. The precise spatial location of these molecules is strongly affected by the regions of hydrophobicity within the extracellular matrix.

Another important consideration in developing a tissue repair scaffold is the promotion of directed cell motility that leads to the formation of new blood vessels. Although some tissues can function with lower capillary densities, adequate perfusion of metabolically active tissue requires intimate localization of parenchymal cells to a dense vasculature in a highly organized manner. For example, the liver has a precisely defined organization in which hepatocytes and microvessels are interdigitated in a highly aligned microarchitecture. In many cases, the degree of order in healing tissue correlates with its functionality. In addition, the architecture of the vasculature itself, e.g., the branching frequency and angles, alignment of vessels, and tortuosity, determines gradients of metabolite exchange and the overall flow fields through the tissue. Therefore, the engineering of such tissues can require approaches to define the geometric architecture of vascular networks for tissue-specific applications.

Certain cell-based pre-vascularization strategies of engineered tissues have utilized randomly seeded cells embedded within a three dimensional matrix. For example, investigators discovered that the speed of vascularization can be increased by allowing endothelial cells to form rudimentary networks in vitro prior to implantation. It has been demonstrated that implantation of scaffolds pre-seeded with endothelial cells facilitates tubulogenesis (the formation of interconnected web-like networks of interconnected endothelial cells) within the scaffold and eventual anastomosis (connection) of the newly formed tubules to host vessels within days.

Unfortunately, such networks are randomly distributed rather than directed. And as described above, the formation of directed complex tissue structures starts with directed cell migration. To date it has been difficult to control the formation and structure of vessels in a fixed and reproducible manner. For example, the random organization of endothelial networks provides no directional guidance to incoming host vessels, often resulting in only an outer shell of the implant becomes perfused, leaving the interior core underperfused. Furthermore, the strict spatial organization of cells, the surrounding extracellular matrix, and vasculature can impact paracrine signaling gradients that define cellular phenotypes and tissue function.

Lastly, surface energy of bulk-scale (>1 mm) materials is a function of three hierarchical structure scales: 1) the fine-scale (<1 micron) molecular structure of a substance, 2) the meso-scale (<50 micron) geometry of the substance surface and 3) the macro-scale (>50 micron) distribution of molecular types (e.g., hydrophilic vs hydrophobic).

The meso-scale is achieved by placing a texture on a surface such as a fiber, membrane, or particle. The phenomenon is known variously as superhydrophobicity, the Lotus effect, and the petal effect. By placing meso-scale shapes, usually the superposition of multiple shapes of different size, can alter the surface energy of a substance independently of its molecular composition. This is an important consideration in applications which would benefit from decoupling the elasticity and stiffness, generally determined by the molecular structure, from the surface energy or hydrophobicity. These textured modifications of a substance provides a second degree of freedom.

It would be advantageous to construct specific structures from biocompatible synthetic or natural polymers, inorganic materials, or composites of inorganic materials with polymers, where the resulting structure has defined pore sizes, shapes and orientations, particularly different pore sizes and orientations within the same device, with more than one surface chemistry, surface energy or texture at different specified sites within the device.

BRIEF SUMMARY OF THE INVENTION

The present disclosure introduces an additional third degree of freedom (macro-scale), and combines the molecular freedom of polymer science with the superhydrophobicity freedom of surface science with the placement freedom of substances and textures using three dimensional printing technology. Without being bound by theory, it is believed that combining all three of these sciences can achieve a synthetic extracellular matrix mimic that capable of directing the proliferation, differentiation and functionalization of cells involved in wound repair.

It is therefore an object of the present invention to provide complex three-dimensional spatial patterns for use in devices of novel design and composition for use in tissue regeneration.

It is another object of the present invention to provide designs and compositions for making complex medical devices of bioerodible or non-bioerodible materials or composites for either cell transplantation or matrix-guided tissue regeneration.

It is a further object of the present invention to provide tissue scaffolds that are the result of high precision printing of implantable medical devices capable of directing cell proliferation, differentiation, apoptosis, and motility.

It is a still further an object of the present invention to produce devices which can selectively encourage the growth of one tissue type over another at specific sites within the matrix by virtue of control of surface chemistry, surface energy, texture or release of growth factor at an intended region of the matrix.

In some embodiments, the present disclosure provides a three-dimensional matrix for tissue regeneration comprising at least three successive layers of at least two biocompatible polymers, the layers arranged to form walls with open voids therebetween, the voids suitable for seeding or ingrowth of cells, the layers comprising a first polymer and a second polymer, and wherein the first and second polymers are disposed in an alternating pattern along at least one axis of the matrix. In some embodiments, the polymers are solid below a temperature of about 36° C. The matrices are useful in a variety of implantable medical devices such as surgical meshes and implantable prosthetics.

The above and other aspects can be achieved as is now described. A printer or raster device is used to lay down small spheres or threads of biomaterials to build by layering a three-dimensional implantable tissue scaffold. The printer device may contain multiple print heads to deliver different biomaterials during the scaffold construction. The biomaterials are delivered in liquid form either as a polymer dissolved in a solvent or as a melt. The spatial precision of the biomaterial placement may be enhanced by electrospinning methods. Electrospinning uses an electrical charge to direct and draw very fine (typically on the micro or nano scale) fibers from a liquid.

The present disclosure provides engineered biomaterials, including patterned biomaterials having organized fiber structures arranged to promote cell motility in a biomimetic extracellular matrix. In certain embodiments, the biomaterials are delivered as continuous fibers. In certain embodiments, the biomaterials are delivered as discrete spheres or drops that combine in liquid form when juxtaposed. In certain embodiments, the patterned biomaterial can include a plurality of different fibers or drops. The patterned biomaterials solidify when they cool or when the solvent evaporates. In certain embodiments, high surface energy biomaterials are organized in clusters or islands within a network of low surface energy biomaterials.

In certain embodiments, the high and low surface energy biomaterials are fibers that are layered in alternating fashion to build walls of mesh or porous structure. In certain embodiments, the patterned biomaterial includes a synthetic extracellular matrix scaffold comprised of a bioabsorbable material. In certain embodiments, the patterned biomaterial can include natural extracellular matrix substances, for example, hyaluronan.

In certain embodiments, the patterned biomaterial can include in combination one or more fibers and one or more clusters or islands of biomaterials.

In certain embodiments, the patterned biomaterial can be deposited on a smooth two-dimensional surface. In certain embodiments, the patterned biomaterial can be deposited on a textured two-dimensional surface, such that when the biomaterial solidifies it acquires a surface texture. The surface texture may be hierarchical, for example, a biomimetic of rose petal.

In certain embodiments, the surface texture may be superhydrophobic possessing a low surface energy. The surface texture may be chosen to encourage certain types of cells to colonize the patterned biomaterial and discourage colonization by other cell types. For example, the surface may encourage motility of endothelial cells and discourage attachment of bacterial cells. In certain embodiments, the surface texture may encourage mechanical integration of the patterned biomaterial with living tissue by inhibiting migration of the patterned biomaterial within a living body. In certain embodiments, one or more chemotaxic substances are embedded on or in the fibers or placed in juxtaposition with the patterned biomaterial. For example, the chemotaxic substances can include, but are not limited to, peptides, proteins, carbohydrates, collagen, fibrin, fibrinogen, matrigel, agarose, polyethylene glycol, dextran, hyaluronic acid, or a combination thereof. In addition, the chemotaxic substance may be a natural substance of botanical origin. For example, any of several constituents of the genus Boswellia, in particular triterpenoids. Preferably, the natural substances are made biocompatible by polymerization with a polyether compound.

In certain embodiments, the method of fabricating a patterned biomaterial includes the placement of soluble fibers or drops wherein after formation of the patterned biomaterial these soluble parts may be removed by dissolution upon contact with a liquid and the insoluble parts remain.

In certain embodiments, channels can be formed in the patterned biomaterial by dissolution. The channels can differ in shape, diameter, and length to generate cellular ingrowth of varying structure. For example, the patterned biomaterial may be entirely solid in the bulk volume of which are disposed soluble cylindrical, bifurcating, Y-shaped, or branching structures. In certain embodiments, the soluble structures can be fabricated into shapes that differ in length, diameter, and density. In certain embodiments, the properties of the soluble structures can be altered to suit a particular application. In certain embodiments, the overall network organization can be defined, for example, by the number and location of branch points, connections, three-dimensional organization, degree of anisotropy, alignment, diameters, lengths, and more.

In certain embodiments, the combination of a bioabsorbable but insoluble portion with a soluble portion can result upon immersion in a liquid a patterned biomaterial comprising one or more wells and/or channels to generate clusters or islands of colonizing cells. In certain embodiments, the islands and/or cluster of colonizing cells can be fabricated into structures that differ in diameter, density, three dimensional organization and shape. In certain embodiments, the properties of the clusters or islands of colonizing cells can be altered to suit a particular application.

In certain embodiments, the patterned biomaterial can be used to treat an ischemic tissue of a subject. For example, the patterned biomaterial can be implanted onto a subject to increase the blood flow to regions of a tissue that are not receiving adequate blood flow. In certain embodiments, pattern biomaterial can be used to treat cardiac ischemia, peripheral vascular disease, or chronic wounds such as diabetic ulcers.

Examples of printing methods include stereo-lithography, selective laser sintering, ballistic particle manufacturing, fusion deposition modeling, directed electrospinning and three dimensional printing. In a preferred embodiment, three-dimensional printing is used to precisely arrange alternating layers of high surface energy and low surface energy fibers in a biomimetic pattern designed to cause cell growth and proliferation in a synthetic matrix that mimics natural extracellular matrix. For example, three-dimensional printing can be used to create a porous bioerodible matrix having interconnected pores or channels, typically between 0.5 and 5 mm, which are separated by walls approximately 100 to 1000 microns thick, the walls constructed of fibers of alternating surface energy and possessing a diameter of approximately 5 to 100 microns.

The macrostructure and porosity of the device can be manipulated by controlling printing parameters, the type of polymer and drop/fiber size, as well as the solvent and/or temperature. In the case of varying the solvent content or temperature, the degree of bonding between fibers or drops can be controlled. Porosity of the matrix walls, as well as the matrix as a whole, can be manipulated using printing methods. Structural elements can be printed in the patterned biomaterial that maintain the integrity of the matrix of an implantable device during resorption in a body. For example, to provide support, the porosity of the walls of the device can be filled with resorbable inorganic material, which can further provide a source of mineral for a repair site of a bone.

Alternatively, one or more of the materials used in the manufacture of the present patterned biomaterial may be a prepolymer in the process of polymerization or polymerizable by application of heat or light, especially UV light.

The use of a prepolymer capable of polymerization at a point of application can form molecular structures different from polymers capable of dissolving in a solvent or melting. In particular, polymers with cross links do not melt and cannot be dissolved in a solvent.

DETAILED DESCRIPTION OF THE INVENTION

Figure 1A:
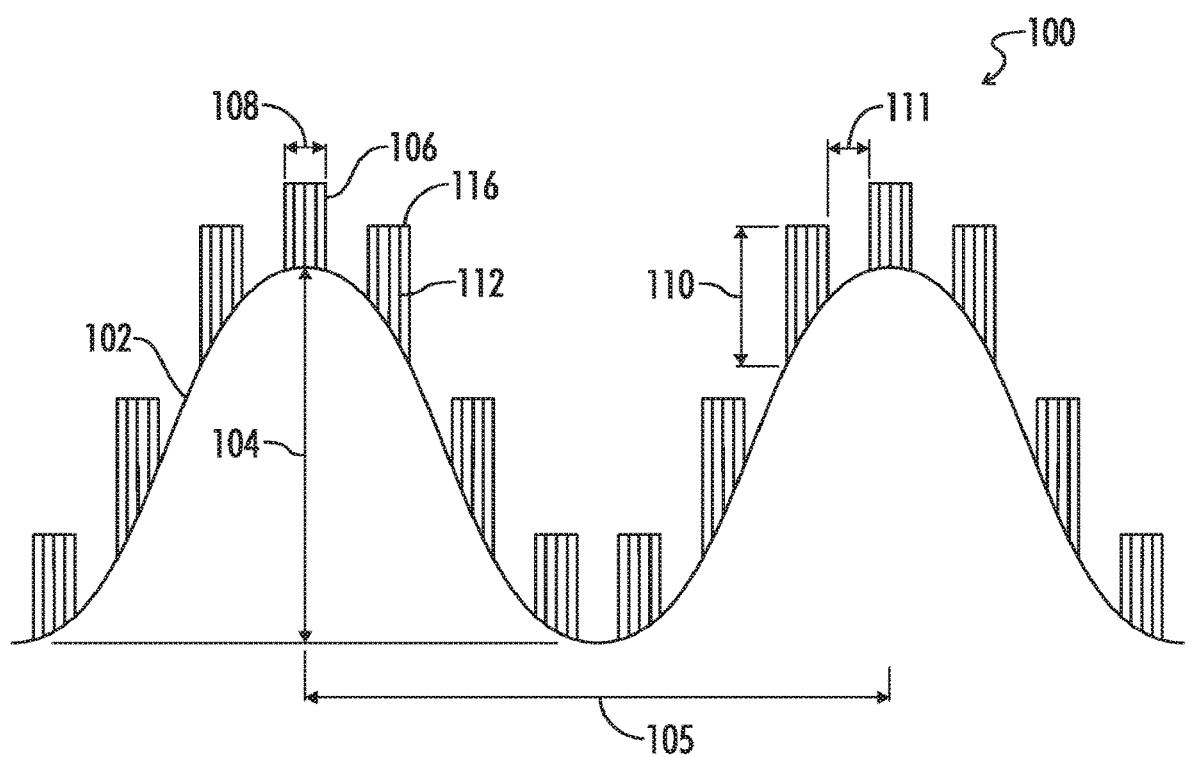
FIG. 1A-1D depicts several views of an exemplary rose surface pattern mimic.

The present disclosure provides engineered biomaterials, including a patterned biomaterial having organized fibers or drops capable of acting as a synthetic extracellular matrix for promoting wound repair.

As used herein, the term "patterned biomaterial" refers to solid naturally-derived and/or synthetic substances that are organized into structures that resemble cylinders, rods, strings, or filaments and networks of such structures.

A matrix of these biomaterials can lead to enhanced integration of these materials into host organisms, wherein host cells can invade or integrate in a manner guided by the architecture and composition of the matrix. This integration can involve blood vessels, thus providing a strategy for enhancing the healing aspects of an implantable prosthetic by allowing for increased vascularization of a wound site. Accordingly, these matrices are particularly useful in surgical applications for mammalian subjects, and in particular, human subjects.

In addition, these patterned biomaterials provide a scaffold for promoting angiogenesis in a host tissue. This integration can also involve other host systems such as the nervous system, muscle, bone, or immune system, and thereby promote new tissue innervation, muscle integration, bone integration, or immune surveillance, respectively. In certain embodiments, a patterned biomaterial of the present disclosure can include chemotaxic substances and additional naturally-derived and/or synthetic scaffolding.

In certain embodiments, the present disclosure provides a patterned biomaterial that encourages cells to organize in clusters, layers and/or lines, in particular bifurcating lines. The bifurcating lines may have a fractal dimension characteristic of capillary networks.

As used herein, the term cell "clusters" and/or "lines" refer to one or more cells, with or without extracellular matrix that are organized in structures that resemble balls, discs, or islands when described as clusters or organized as interconnected filamentary networks when described as lines.

The patterning of the biomaterial can be used in conjunction with bioactive or chemotaxic agents, such as paracrine factors. These bioactive agents act to modulate how host tissue and cells respond to the patterned biomaterial. In certain embodiments, a duster or line of the present disclosure can include cells and a naturally-derived and/or synthetic scaffolding of the present invention in combination.

In certain embodiments, the patterned biomaterial of the present invention is used to repair soft tissue during a surgical procedure. There is a need to encourage the formation of functional tissue as opposed to the usual formation of scar tissue. Functional tissue is associated with fewer adverse events, and is capable of self-repair. Scar tissue serves a short term function in joining tissue together, but generally is remodeled by the body. The remodeling process can result in the surgical repair failing post-surgically, as is common in hernia repairs.

Functional tissue requires blood supply, unlike scar tissue which is generally sparsely populated with vessels or avascular. Accordingly, there is a need for a soft tissue repair device for inducing angiogenesis, the formation of new blood vessels, in a controlled fashion within organized three dimensional tissue constructs. There is also a need to induce blood vessel formation of a tissue in a subject that does not receive adequate blood flow. The present disclosure addresses this need by engineering a patterned biomaterial that mimics natural extracellular matrix by providing a substrate on which cells are motile. In this sense, the patterned biomaterial acts as a scaffold that possesses high surface energy and low surface energy regions that geometrically direct the formation of functional constructs of cells.

The patterned biomaterials of the present disclosure promote the rapid formation of vessels that are spatially delineated, providing novel approaches to vascularizing issues formed by the body during wound repair. These patterned biomaterials are also useful in treating ischemic diseases, and promoting tissue healing and integration at sites normally undersupplied with blood.

Implantation of patterned biomaterial into a subject can lead to engraftment, remodeling of the local microenvironment, anastomosis, and formation of stable capillaries within an implanted scaffold that directs blood vessels and blood flow. By employing synthetic materials with geometrically controlled distributions of clusters and lines of high and low surface energy, the subsequent formation of blood vessels in vivo is able to be spatially controlled.

The arrangement of fibers of different surface energy into patterned networks of the present disclosure provides a means to support rapid invasion and integration of host vasculature into the device to generate perfused, functional blood vessels by providing a pre-specified architecture as a template in which the new blood vessels mirror the architecture of fibers of the implanted tissue scaffold. The architecture of the fibers of a patterned biomaterial can also encourage certain types of cellular infiltrates. For example, in certain cases endothelial cells are promoted and in other cases fibroblasts are encouraged, and in still another case the distribution and densities of combinations of cell types are promoted.

The material and geometry of the patterned biomaterial defines the in vivo architecture of the blood vessels, connective tissue, muscle tissue and anchoring networks that are preferred in the post-operative functional healing of a wound site. Because these patterned networks act as templates for the formation of blood vessels, benefit the motility of invading host tissue, directs their rate of propagation and spatial distribution they can rationally impact the rate and extent of host cell integration, and thus be used as a means to direct revascularization from a well perfused site to reach into and support ischemic tissues. In certain embodiments, the pattern biomaterial is resorbable such that the original matrix can be partially or entirely replaced by host cells and tissue, with the architecture of the patterned biomaterial being templated and preserved by the new host tissue.

This use of patterning technology in combination with variations in composition that determine rates of resorption and surface energy values is novel in that such a construct mimics the composition of natural extracellular matrix. Accordingly, such a synthetic biomaterial possesses some of the same functionality as extracellular matrix regarding the organization of infiltrating cells at an implant site for controlling the ultimate in vivo composition and distribution of tissue types. Functional promotion and patterning of cells and subsequent formation of vessels in vivo constitutes a significant technical advance within the field of surgical medicine.

In some embodiments, the present disclosure provides a three-dimensional matrix for tissue regeneration comprising at least three successive layers of at least two biocompatible polymers, the layers arranged to form walls with open voids therebetween, the voids suitable for seeding or ingrowth of cells, the layers comprising a first polymer and a second polymer, and wherein the first and second polymers are disposed in an alternating pattern along at least one axis of the matrix. The first polymer can be hydrophobic and the second polymer can be hydrophilic. In other embodiments, the first polymer is lipophilic and the second polymer is hydrophilic. The first and second polymers can be nanofibers having a diameter ranging from 100 nm to 5 microns or 100 nm to 1 micron or 100 nm to 500 micron. Useful hydrophobic polymers include without limitation polypropylene, polycaprolactone, and polylactic acid. Useful hydrophilic polymers include without limitation polyether urethanes, polyester urethanes, or polyhyaluronic acid.

In some embodiments, the nanofibers are arranged as stacked layer such that they form wherein the walls that intersect at junctions along parallel first axes, such as in a grid pattern. The first and second polymers may be disposed in an alternating pattern along the first axes, or they may be disposed in an alternating hydrophilic-hydrophobic pattern along a second axes that are perpendicular to the first axes.

The layers may further include surface pattern is provided on one or more layers of said device.

The surface energy is advantageously affected by the alternating hydrophobic-hydrophilic pattern. Additionally, the surface energy can be advantageously be affected by including a surface pattern such that the surface energy is varied on at least three spatial scales comprising 1) a macro scale ranging from 50 micron to 1 mm obtained by forming layers of polymers of different surface energy, 2) a meso scale ranging from 1 micron to 50 micron obtained by placing a surface pattern on the polymers, and 3) a fine-scale of less than 1 micron obtained by variation of molecular structure.

The present disclosure further provides a three-dimensional medical device comprising the matrices disclosed herein, wherein the matrix is formed on an implantable layer such that the final three-dimensional device comprises the matrix joined to an implantable layer. In some embodiments, the layer and the matrix are bioabsorbable, and wherein the layer bioabsorbs more rapidly than the matrix.

In another embodiment, a matrix for tissue regeneration comprises at least three successive layers of at least two biocompatible polymers the layers arranged as loops having open voids therebetween, the voids suitable for seeding or ingrowth of cells, the layers comprising a first polymer and a second polymer, wherein the first and second polymers are disposed as interlocking loops, and the first and second polymers are arranged in an alternating pattern. The first polymer can be hydrophobic and the second polymer can be hydrophilic. In other embodiments, the first polymer is lipophilic and the second polymer is hydrophilic. The first and second polymers can be nanofibers having a diameter ranging from 100 nm to 5 microns or 100 nm to 1 micron or 100 nm to 500 micron. Useful hydrophobic polymers include without limitation polypropylene, polycaprolactone, and polylactic acid. Useful hydrophilic polymers include without limitation polyether urethanes, polyester urethanes, or polyhyaluronic acid.

The layers may further include surface pattern is provided on one or more layers of said device.

The surface energy is advantageously affected by the alternating hydrophobic-hydrophilic pattern. Additionally, the surface energy can be advantageously be affected by including a surface pattern such that the surface energy is varied on at least three spatial scales comprising 1) a macro scale ranging from 50 micron to 1 mm obtained by forming a portion of said loops from a polymer of a surface energy different from the surface energy of the remaining said loops formed from a second polymer, 2) a meso scale ranging from 1 micron to 50 micron obtained by placing a surface pattern on the polymers, and 3) a fine-scale of less than 1 micron obtained by variation of molecular structure.

The aforementioned matrix may be formed on an implantable layer such that the final three-dimensional device comprises the matrix joined to an implantable layer. In some embodiments, the layer and the matrix are bioabsorbable, and wherein the layer bioabsorbs more rapidly than the matrix.

In another embodiment, a three-dimensional matrix for tissue regeneration comprises at least three successive layers of at least two biocompatible, the layers arranged in a series of stacked triangles, the triangles providing open voids, the voids suitable for seeding or ingrowth of cells, the layers comprising a first polymer and a second polymer, and wherein the first and second polymers are disposed in an alternating pattern along at least one axis of the matrix. The triangles are in some embodiments superimposed on one another such that that the superimposition of triangles (here 9) does create various quadrangles, pentagons and a hexagon in some embodiments, the matrix comprises at least nine layers of triangles of varying sizes, and substantially replicates a sri yantra pattern.

Three Dimensional Printing

Suitable devices include both those with a continuous jet stream print head and a drop-on-demand stream print head. In the former case, a line of polymer is directed. In the second case, a drop of polymer is directed. A high speed printer of the continuous type, for example, is the Dijit printer made and sold by Diconix, Inc., of Dayton, Ohio, which has a line printing bar containing approximately 1,500 jets which can deliver up to 60 million droplets per second in a continuous fashion and can print at speeds up to 900 feet per minute.

Both raster and vector apparatuses can be used. A raster apparatus is where the print head goes back and forth across the bed with the jet turning on and off. This can have problems when the material is likely to clog the jet upon settling. A vector apparatus is similar to an x-y printer. Although potentially slower, the vector printer may yield a more uniform finish.

The object of three-dimensional printing is to create a solid state object by ink-jet printing a binder into selected areas of sequentially deposited layers of powder. In the present disclosure, this process is modified in that powder is not required. The drop or line that is initially liquid becomes a volumetric solid when deposited on a surface. In this sense, the process is more like ink in an ink-jet printing process, where a third dimension is created by the creation of successive layer of deposited polymer.

Instructions for each layer can be derived directly from a computer-aided design (CAD) representation of the patterned biomaterial. The area to be printed is obtained by computing the area of intersection between the desired plane and the CAD representation of the object. A first layer is joined to a second layer by the liquid state of the polymer being deposited during the time of creation of the second layer. The liquid state of the second layer partially melts or dissolves into the first solid layer to form the three dimensional structure in successive layers.

While the layers become hardened or at least partially hardened as each of the layers is laid down, once the desired final biomaterial configuration is achieved and the layering process is complete, in some applications it may be desirable that the form and its contents be heated or cured at a suitably selected temperature to further promote binding of the discrete lines or drops.

Construction of a three-dimensional component by printing can be viewed as the knitting together of structural elements, e.g., drops or lines. These elements are called microstructural primitives. The dimensions of the primitives determine the length scale over which the microstructure can be varied. Thus, the smallest region over which the surface energy of the patterned biomaterial can be varied has dimensions near that of individual microstructural primitives. Droplet primitives have dimensions that are very similar to the width of line primitives, the difference is whether the material is laid down in a continuous line or discrete drops. The dimensions of the line primitive depend on the polymer viscosity and surface tension. A line primitive of 10 micron width is in certain cases possible, more typically the dimension is 40-60 microns. Higher print head velocities and lower polymer viscosity produce finer lines.

When solvents are used, the drying rate is an important variable in the production of patterned biomaterials by three-dimensional printing. Very rapid drying of the solvent tends to cause warping of the printed component. Much, if not all, of the warping can be eliminated by choosing a solvent with a low vapor pressure. For example, patterned biomaterials prepared by printing with a solution of polymer and chloroform have nearly undetectable amounts of warpage, while large parts made with methylene chloride exhibit significant warpage. It has been found that it is often convenient to combine solvents to achieve minimal warping and adequate bonding between the particles. Thus, an aggressive solvent can be mixed in small proportions with a solvent with lower vapor pressure.

Ballistic Particle Manufacturing (BPM) and Fusion Deposition Modeling (FDM)

Ballistic particle manufacturing is in some respects more like the present methods of printing than the traditional powder-based three-dimensional printing method, although both can be adapted to the manufacture of the present patterned biomaterial. Ballistic particle manufacturing uses an ink-jet printing apparatus wherein an ink-jet stream of liquid polymer or polymer composite material is used to create three-dimensional objects under computer control, similar to the way an ink-jet printer produces two-dimensional graphic printing.

A patterned biomaterial device is formed by printing successive cross-sections, one layer after another, to a target using a cold welding or rapid solidification technique, which causes bonding between the drops and the successive layers of drops.

Fusion deposition modeling employs an x-y plotter with a z-direction motion to position an extrudable filament formed of a polymeric material, rendered fluid by heat or the presence of a solvent. A suitable system is available from Stratasys, of Minneapolis, Minn.

Ballistic particle manufacturing, fusion deposition modeling and three-dimensional printing are related in the sense that all three approaches control the deposition of matter in small areas. This aspect is advantageous in the present application to the extent that local composition can be specified and constructed for any desired three-dimensional profile. The composition control is only limited by the resolution of the particular apparatus used for construction.

Fusion deposition modeling builds structures by extruding a fine filament of plastically deformable material through a small nozzle. The nozzle is directed over the built surface by appropriate x, y and z motion control so as to yield the desired three dimensional structure. Similarly, ballistic particle manufacturing involves motion control of an ink jet print head to deposit matter in the form of small droplets. Appropriate control of where the droplets are printed permits the construction of a desired three dimensional shape. Three-dimensional printing uses two sources of material: the material that makes up the porous layer and the material that is printed. All three are adaptable to manufacture of the present patterned biomaterial, each with distinct advantages regarding the chosen architecture biomaterial architecture.

Local composition control using fusion deposition modeling and ballistic particle manufacturing requires the application of multiple printing or extrusion heads. A similar approach can be followed with three-dimensional printing by using multiple print-heads. Alternatively, multiple droplets may be printed into the same location when using three-dimensional printing to increase the local composition of the species contained in the printed solution.

Selection of Polymers

The printing method of the patterned biomaterial relies on the polymer constituents being in a liquid phase. The liquid phase is typically realized by dissolution of a solid polymer in a solvent or by melting. In the case of a melt phase, it is preferable to select polymers having relatively low melting points, to avoid exposing resorbable polymers to elevated temperatures. Resorbable polymers are typically susceptible to thermal degradation.

A number of polymers are commonly used in the construction of implantable medical devices. Unless otherwise specified, the term "polymer" will be used to include any of the materials used to form the patterned biomaterial matrix, including polymers and monomers which can be polymerized or adhered at point of application to form an integral unit.

In a preferred embodiment the microstructural elements are formed of a polymer, such as a synthetic thermoplastic polymer, for example, ethylene vinyl acetate, poly(anhydrides), polyorthoesters, polymers of lactic acid and glycolic acid and other a hydroxy acids, and polyphosphazenes, a protein polymer, for example, albumin or collagen, or a polysaccharide containing sugar units such as lactose.

In a more preferred embodiment the polymers are absorbable polyurethane containing lactide diol blocks capable of resorbing in vivo. The lactide diol blocks are linked with ethylene diols and/or propylene diols via urethane or urea links. By varying the proportion of ethylene diol to propylene diol, as well as the choice of the linking diisocyanate, the surface energy of the resulting polymer can be modified to achieve a desired specification. Generally, these molecules are called polyester polyurethanes or polyesterurethanes.

An example of a polyesterurethane is an aliphatic polyester based polyesterurethane consisting of poly(l-lactic acid) and poly(ethylene succinate) prepared via chain-extension reaction of poly(l-lactic acid)-diol and poly(ethylene succinate)-diol rusing 1,6-hexamethlyene diisocyanate as a chain extender. The poly(l-lactic acid)-diol is synthesized by direct polycondensation of l-lactic acid in the presence of 1,4-butanediol.

Poly(ethylene succinate)-diol can be synthesized by condensation polymerization of succinic acid with excessive ethylene glycol.

The polymer can be non-biodegradable or biodegradable, typically via hydrolysis or enzymatic cleavage. In the case of polymers for use in making devices for cell attachment and growth, polymers are selected based on the ability of the polymer to elicit the appropriate biological response from cells, for example, attachment, migration, proliferation and gene expression.

An alternative material is a polyester in the polylactide/polyglycolide family. These polymers have received a great deal of attention in the drug delivery and tissue regeneration areas for a number of reasons. They have been in use for over 30 years in surgical sutures, are Food and Drug Administration (FDA)-approved and have a long and favorable clinical record. A wide range of physical properties and degradation times can be achieved by varying the monomer ratios in lactide/glycolide copolymers: poly-L-lactic acid and poly-glycolic acid exhibit a high degree of crystallinity and degrade relatively slowly into shards. Copolymers of poly-L-lactic acid and Poly-glycolic acid are amorphous and rapidly degraded into a gel state. The advantage of the polyesterurethane polymers over the polyester polymers is that the former degrade both into a gel state and are true surface-eroding polymer. As a consequence polyesterurethanes have a preferred degradation state while retaining for a longer period the original patterns of the biomaterial. However, there are applications where each are preferred.

In some embodiments, non-polymeric materials can also be used to form the matrix either alone or in combination with a polymer. Examples include organic and inorganic materials such as hydoxyapatite, bone-derived apatite, calcium carbonate, other bone substituting agents, buffering agents, and lactose, as well as other common excipients used in drugs, which are solidified by application of adhesive rather than solvent.

The selection of the solvent for chemotaxic agents delivered on a resorbable polymer matrix depends on the desired mode of release of the chemotaxic agent. In the case of a totally resorbable device, a solvent is selected to deliver the chemotaxic agent alone and when delivered dissolves the deposited polymer matrix or is selected to contain a second polymer which is deposited along with the chemotaxic agent.

In the first case, the printed chemotaxic droplet locally dissolves the underlying polymer matrix and begins to evaporate and thus is adherent to the surface of the immediate underlying polymer matrix layer. In the second case, the drug is effectively deposited in the a second polymer matrix after evaporation since the dissolved polymer is deposited along with the chemotaxic agent. The first case releases the chemotaxic agent rapidly and creates the highest concentration gradient when placed in vivo. The second case releases the chemotaxic agent more slowly since release depends in part of the resorption of the carrier polymer. In this second case, the concentration of chemotaxic agent is more uniform and constant over time.

The solvent evaporation rate is primarily determined by the vapor pressure of the solvent. There is a range from one extreme over which the polymer is very soluble, for example, 30 weight percent solubility, which allows the polymer to dissolve very quickly, during the time required to print one layer, as compared with lower solubilities. The degree to which prior layers are dissolved during application of a subsequent layer depends on the solubility of the polymer in the solvent. Fine fibers are more completely dissolved than fibers with larger diameters.

Polymer Concentration

In general, microstructural element are a resorbable polymer such as polyesterurethane or polyester of molecular weight 5,000-200,000, in a solvent such as chloroform or a mixture of chloroform and a less-volatile solvent such as ethyl acetate to minimize warping. The surface energy of these can be varied by varying the proportion of hydrophilic and hydrophobic blocks in the polymer. Alternatively, a different polymer may be used such as poly-lactic acid, poly-glycolic acid or polycaprolactone.

The polymer concentration in a microstructural element solution will generally be at the limit of what can be accommodated by the nozzle, both to maximize the amount of solid polymer delivered and to minimize migration of the solvent away from the point of application in the formation of a patterned biomaterial. Reduced solvent migration increases the resolution of the microstructural elements of prior deposited layers, e.g., reduces swelling or geometrical slumping.

The upper limit of polymer concentration is 15% for poly-L-lactic acid of 100,000 MW. This concentration of polymer may in some cases make printing of commercially viable devices impossible. The cases where the polymer is sparingly soluble, a filler may be used. Microstructural element volume can be increased by including small cross-linked or otherwise less soluble particles in the printing solution.

For example, polyglycolic acid is not soluble in chloroform or ethyl acetate. Nanoparticles of crosslinked polyesterurethane can be included in the printing solution (particles up to microns in diameter can be accommodated through most nozzles) to increase the polymer content which is printed.

The amount of matter which is printed into the biomaterial can also be increased by including small inorganic particles in the polymer solution, for example, bone derived apatite.

Surface Texture Considerations

The manner in which the microstructural elements are laid down determines a surface texture between these elements. There is a first distinction in surface texture achieved by the dimensions of the microstructural elements. There are two principal modes: a droplet configuration and a line configuration. Drops are discrete in three dimensions, whereas lines are discrete in two dimensions.

In the droplet mode the drops can be spaced apart in on a surface, and they can be joined together by a subsequent layer of drops in staggered form, or joined together by a line. The drops can be spaced closer together to slightly touch, creating an undulating profile, or they can be placed in close proximity so that they effective merge before solidifying. In the creation of islands, they can be stacked in pyramid fashion in a vertical direction.

In the line mode the lines are generally laid down in alignment with the previous line. However draping configurations can be achieved. For example, a partial wall can be formed of several aligned lines on top of which a line is placed such that it crosses this partial wall in undulatory fashion, such that adhesion between the wall and the line is only at points. After solidification, these draping feature typically are free to move away from the established wall structure. Draping features can be placed at points intermediate during the formation of a complete wall. In addition, a partial wall can be fenestrated by subsequent layers of droplets built up to form the edges of windows, the top edge of which is closed by the subsequent addition of lines. These lines typically will droop down into the established fenestrations. By varying the deposit speed of the final lines one can create a multiplicity of drooping lines into the fenestration of different lengths creating a curtain of drooping lines.

Alternatively the microstructural elements can be deposited on a plane with a mold pattern. For example, the mold pattern can be a superhydrophobic pattern capable of generating a Wenzel-Cassie effect or a Wenzel-Baxter effect. Other surface textures can be achieved by incorporating on or in deposited microstructural element a variety of solid particulate. The solid particulate may be a permanent nanostructure, such as a nanotubule, a bucky ball, or any of variously known nanoparticulate geometries. The solid particulate may be soluble, such that when the patterned biomaterial is placed in a solvent the particulate are partially or entirely removed without affecting the remaining portion of the biomaterial.

In addition, directed and random writing techniques can be combined. For example, at various points during the construction of a directed structure a spray or electrospinning technique could be employed to deposit randomly oriented fibrous or particulate masses.

Bioactive Agents

There are essentially no limitations on the bioactive agents that can be incorporated into the patterned biomaterials, although those agents which produce a chemotaxic effect are most desirable in wound healing or tissue scaffolding applications. Bioactive agents need not be incorporated as a liquid, they can be processed into particles using spray drying, atomization, grinding, or other standard methodology, or those agents which can be formed into emulsifications, microparticles, liposomes, or other small particles, and which remain stable chemically and retain biological activity in a polymeric matrix, are useful.

Examples of chemotaxic agents generally include proteins and peptides, nucleic acids, polysaccharides, nucleic acids, lipids, and non-protein organic and inorganic compounds. Examples of other bioactive agents have biological effects including, but not limited to, anti-inflammatories, antimicrobials, anti-cancer, antivirals, hormones, antioxidants, channel blockers, and vaccines. It is also possible to incorporate materials not exerting a biological effect such as air, radiopaque materials such as barium, or other imaging agents.

In a preferred embodiment for tissue regeneration matrices, cell growth, differentiation, and/or migration modulators are incorporated into specific regions of the device at the same level of resolution as the pores and channels. These may act in combination with surface texture, surface energy, and overall shape and distribution of the microstructural elements to achieve an extracellular matrix mimic with controllable tissue directing functionality.

Of particular interest are surface-active agents which promote cell adhesion, such as an RGD peptide, or a material which inhibits cell adhesion, such as a surfactant, for example, polyethylene glycol or a Pluronic (polypropylene oxid-polyethylene oxide block copolymers).

For example, it may be desirable to incorporate adhesion peptides such as the RGD adhesion peptide into certain channels (e.g., those for blood vessel ingrowth). An adhesion peptide, such as the peptide having a hydrophobic tail marketed by Telios (La Hoya, Calif.) as Peptite, can be dissolved in water and deposited onto the surfaces of pores in the patterned biomaterial.

The surface can be modified to prevent cellular adhesion. This may be desirable to prevent excessive soft connective tissue ingrowth into the device from the surrounding tissue, and can be accomplished, for example, by depositing an aqueous solution of a pluronic or poloxamer in the voids. The hydrophobic block of such copolymers will adsorb to the surface of the channels, with the hydrophilic block extending into the aqueous phase. Surfaces with adsorbed pluronics resist adsorption of proteins and other biological macromolecules.

In certain embodiments, the patterned biomaterial can contain one or more of bioactive substance(s) including, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-.alpha. (TGF-.alpha.), TGF-.beta.1, TGF-.beta.2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). For example, the patterned biomaterial can include a biologically effective amount of VEGF.

Porosity

Porosity is a void in the patterned biomaterial that bridges two sides of the device. Porosity of printed biomaterials can be created either at the level of the microstructural element size or at a macroscopic size (>1 mm). At the level of the microstructural size, porosity is controlled by where the elements are placed, and thus pore size and shape can vary in three dimensions.

Porosity at a sub-element size level can be created in a variety of ways. Printing a polymer solution onto a bed of fibers which are not soluble in the polymer solution and too large in one dimension to be printed and which can be subsequently dissolved with a solvent that doesn't affect the polymer can create pores. Alternatively, the polymer solution can be deposited onto a bed containing a foaming agent. Alternatively, the polymer solution can be deposited on a heated bed that caused the solvent to pass into the gaseous phase before leaving the polymer, thus creating gaseous voids in the polymer, some of which may be inter-connected.

Patterned Biomaterials Comprising Living Cells

In certain embodiments, the patterned biomaterial can be seeded with cells. In certain embodiments, the patterned biomaterial can be comprised of one or more cell types. Cells can confer tissue functionality and provide structures, which can replace or facilitate the repair of a tissue of the subject. For example, the patterned biomaterial can include, but is not limited to, muscle cells to provide contractile structures, vascular and/or neural cells to provide conductive elements, metabolically active secretory cells, such as liver cells, hormone synthesizing cells, sebaceous cells, pancreatic islet cells or adrenal cortex cells to provide secretory structures, stem cells, such as bone marrow-derived or embryonic stem cells, dermal fibroblasts, in keratinocytes, Schwann cells for nerve implants, smooth muscle cells and endothelial cells for vessel structures, urothelial and smooth muscle cells for bladder/urethra structures and osteocytes, chondrocytes, and tendon cells for bone and tendon structures, or a combination thereof. In certain embodiments, the patterned biomaterial can include other cell types including, but not limited, to hepatocytes and chondrocytes.

Cells suitable for inclusion in the patterned biomaterial of the present disclosure can be derived from any suitable source. The subject, which may be a mammalian subject, particularly a human subject, to receive the implant of the patterned biomaterial of the present disclosure can determine the source of the cells to be included in the patterned biomaterial. In certain embodiments, the cells can be derived from an autologous source. For example, the cells can be derived from the subject to be implanted with the patterned biomaterial. For example, epithelial cells can be derived from the skin of the subject to be implanted with the patterned biomaterial. In certain embodiments, the cells can also be generated from stem cells derived from various sources that are then differentiated into the desired cell type. For example, the stem cells can be derived from the subject to be implanted with the patterned biomaterial. In certain embodiments, cells can be cultured for a period of time under various conditions to induce certain phenotypes before placing the cells in the patterned biomaterial.

Applications Using the Patterned Biomaterials

In certain embodiments, the patterned biomaterial of the present disclosure can be implanted in a human subject. For example, in certain embodiments, the patterned biomaterial of the present disclosure can be implanted in a subject by suturing the patterned biomaterial to fat pads or muscle tissue in the lower abdomen.

In certain embodiments, the patterned biomaterial of the present disclosure can be used to enhance vascularization in ischemic settings, such as, by acting as an angiogenic tissue scaffold to promote neovascularization and ultimately increase blood flow to regions of tissues that are not receiving sufficient blood supply. In certain embodiments, the patterned biomaterial of the present disclosure can be implanted in a region of a subject that requires an increase in blood flow. For example, the patterned biomaterial can be implanted in and/or near an ischemic tissue. In certain embodiments, the patterned biomaterial can be implanted to treat cardiac ischemia. The patterned biomaterial can be implanted to revascularize from healthy coronary circulation or neighboring non-coronary vasculature.

In certain embodiments, the patterned biomaterial of the present disclosure can be used as a novel adjunct to coronary artery bypass grafting (CABG) in addressing cardiac ischemia. In certain embodiments, during CABG surgery, a surgeon can apply the patterned biomaterial of the present disclosure across regions of incomplete reperfusion. For example, the patterned biomaterial can be placed in order to revascularize from healthy coronary circulation or neighboring non-coronary vasculature (such as circulation from the left internal mammary artery) into the ischemic zone unlikely to be addressed by the CABG procedure.

In certain embodiments, the patterned biomaterial can be used to direct neovascularization around a section of an artery subject to reduced blood flow or occlusion. In this case, the patterned biomaterial can be used to promote revascularization of a region of ischemic myocardium in addition to a CABG procedure.

In many patients that suffer from acute myocardial ischemia and in another even larger cohort of patients with untreatable coronary disease, there remain areas of viable heart that do not naturally revascularized but can be revascularized by an angiogenic tissue scaffold. In certain embodiments, the patterned biomaterial can potentially revascularize those inaccessible ischemic zones in these patients. The selection of an alternating hydrophobic/hydrophilic arrangement of fibers of the patterned biomaterial can stimulate and spatially direct revascularization by directing blood flow from nearby unobstructed coronary vasculature to around and beyond a coronary obstruction leading to micro-perfused distal myocardium to protect cardiomyocytes viability and function.

The patterned biomaterial of the present disclosure can enhance neovascularization as well as influence vascular architecture through two potential mechanisms. The patterned biomaterial can be incorporated into existing capillary beds to increase blood flow. Second, the patterned biomaterial can deliver extracellular matrix constituents and secrete growth factors into tissue thereby providing a microenvironment that promotes angiogenesis.

The patterned biomaterials disclosed herein are meshes comprising polymeric nanofibers. The hydrophilic and hydrophobic nanofibers are used to construct the mersh, such that the hydrophilic and hydrophobic nanofibers are disposed in alternating patterns, thereby affecting the surface energy of the matrix and affect cell growth and healing. In all of the embodiments disclosed throughout, the hydrophobic fibers may be a hydrophobic polymer, including but not limited to polypropylene, polycaprolactone, and polylactic acid. Hydrophilic fibers may be hydrophilic polymers, including but not limited to polyether urethanes, polyester urethanes, or polyhyaluronic acid.

The patterned biomaterial of the present disclosure is capable of enhancing neovascularization by spatially guiding the invading sprouts of an angiogenic capillary network upon implantation, without incorporation into the nascent vessels. The patterned biomaterial of the present disclosure can be used in conjunction with various types of engineered tissue constructs to aid in the vascularization of ischemic tissue.

In certain embodiments, the patterned biomaterials of the present disclosure can be useful in other applications in which it would be beneficial to have an engineered material to aid in spatially guiding the direction of host cell and tissue invasion. Such applications can include, but are not limited to, nerve regeneration. In certain embodiments, the patterned biomaterial can be seeded with a heterotypic cell suspension. For example, for nerve regeneration applications, the cell suspension can include neurons, neuronal stem cells, or cells that are associated with supporting neuronal function, or a combination thereof. In certain embodiments, the patterned biomaterial can be used at a site of tissue damage, e.g., neuronal tissue damage.

In certain embodiments, the patterned biomaterial of the present disclosure can allow for maintenance of the viability and proper function of a surgical repair site. For example, the patterned biomaterial can allow for maintenance of the viability and proper function of muscle tissue surrounding a hernia repair.

In certain embodiments, the patterned biomaterial of the present disclosure can enhance wound healing. In certain embodiments, the patterned biomaterials can be useful in the treatment of chronic wounds such as, for example, diabetic foot ulcers. Additionally, the patterned biomaterial of the present disclosure can be useful in the treatment of wounds sustained during military combat. In certain embodiments, the patterned biomaterial can be implanted in a subject to treat peripheral vascular disease, diabetic wounds, and clinical ischemia.

In certain embodiments, the patterned biomaterial of the present disclosure can be used to enhance repair of various tissues. Examples of tissues that can be treated by the patterned biomaterial of the present disclosure includes, but is not limited to, skeletal muscle tissue, skin, fat tissue, bone, cardiac tissue, pancreatic tissue, liver tissue, lung tissue, kidney tissue, intestinal tissue, esophageal tissue, stomach tissue, nerve tissue, spinal tissue, and brain tissue.

In certain embodiments, a method of vascularizing a tissue of a subject includes providing a patterned biomaterial comprising endothelial cells organized along lines and implanting the patterned biomaterial into a tissue of the subject, wherein the biomaterial promotes increased vascularity and perfusion in the subject.

To facilitate a better understanding of the present disclosure, the following examples of certain aspects of some embodiments are given. In no way should the following examples be read to limit, or define, the entire scope of the disclosure.

EXAMPLES

Example 1: Polymer

Polymers suitable for constructing patterned biomaterials of the present disclosure are preferably absorbable in situ. Polyesterurethanes are polyurethanes copolymerized with a lactide diol. Lactide diol was prepared using the following materials: 1,6-Hexanediol (Acros), Toluene (Acros) D,L-Lactide (SAFC), L,L-Lactide (Aldrich), Tin-ethylhexanoate (Sigma Aldrich), Chloroform (Sigma Aldrich), Diethylether (Sussmann)

This procedure is to be performed in closed vessels purged continuously with cryogenically distilled (dry) argon or nitrogen.

30 grams of 1,6-hexanediol is to be placed in 600 ml of toluene in a graduated 2 Liter flat bottom flask equipped with a magnetic stir rod. The flask is to be capped with a 2-hole stopper, one hole equipped with an input conduit and the other hole equipped with an output conduit connected to an oil trap (to prevent back flow of water vapor). The input conduit is to be connected to the nitrogen source and nitrogen flowed at approximately 5 Liters per hour. The flask is to be placed on a magnetic stirrer/hot top combination.

The toluene solution is to be stirred while raising the solution temperature to 70° C., and thereafter in 10° C. increments until the hexanediol is completely dissolved. Upon dissolution, the solution volume is to be noted. Temperature and nitrogen flow is to be continued until the solution volume drops by 150 ml. Temperature can be raised to 130° C. to facilitate toluene vaporization.

A sample of the solution is to be retrieved by syringe (to avoid contact with humid air), and the toluene removed by vacuum evaporation. A Karl Fischer water content measurement is to be performed on the solid hexanediol. The above distillation procedure is to be continued until the water content is <300 ppm H2O by weight. The solution is to be cooled and stored under nitrogen.

Using the above setup, 150 grams of D,L-lactide and 150 grams of L,L-lactide are to be dissolved in 1750 ml of toluene by heating to 115° C., while stirring under nitrogen flow. Upon dissolution the solution volume is to be noted and the temperature is to be raised to 130° C. The nitrogen flow is to be continued until 400 ml of toluene is removed.

A sample of the solution is to be retrieved by syringe (to avoid contact with humid air), and the toluene removed by vacuum evaporation. A Karl Fischer water content measurement is to be performed on the solid hexanediol.

The above distillation procedure is to be continued until the water content is <300 ppm H2O by weight. The solution is to be cooled and stored under nitrogen.

Weigh an appropriately sized flask (4 L). Note flask weight, preferably the weight includes a closure or the stopper with closed conduits disconnected. The hexanediol and lactide solutions are to be combined in the weighed flask, connected to nitrogen flow and stirred. The combined solution is to be heated in 10° C. increments to 70° C.

After 15 minutes, 600 mg of tin ethylhexanoate is to be added drop-wise using a 1 cc syringe, while stirring vigorously. The temperature of the solution is to be raised to 120° C. in 10° C. increments. [if a temperature controlled heating mantle is used, the temperature rise will be sufficiently slow that the 10° C. heating increment can be ignored.]

Turn off the nitrogen flow while keeping conduits connected such that the solution volume is closed from contact with air. While stirring and heating, react for 5 hours. Add an additional 400 mg of tin ethylhexanoate. Flush with nitrogen. Continue for an additional 3 hours. Add an additional 400 mg of tin ethylhexanoate. Flush with nitrogen. Continue for an additional 11 hours at 120° C. Reduce solution temperature to 70° C. Connect the output port of the oil trap to a vacuum source. Stop stirring and heat until toluene is removed.

Discontinue vacuum. Add 800 ml of dry chloroform flush with nitrogen, stir at 70° C. until the solid is completely dissolved. The resulting turbid solution is to be filtered using a 0.2 micron PTFE filter. Remove the solvent from the filtrate under vacuum.

A sample of the dried solid is to be measured for water content using Karl-Fischer. The water content is to be <300 ppm. If not within this specification, the solid can be dried by chloroform distillation.

Preparation of Polyesterurethane

Polyesterurethane is prepared from the following materials: IPDI (Isophorone diisocyanate) 202.9 mmol, 1,4-Butanediol 142.8 mmol, Toluene 2000 mL, Dibutyltin dilaurate 11.6 mmol, PTMG 2000 (Terathane 2000) 20.1 mmol, PLA Diol AP1756 40.3 mmol. All operations are to be performed under nitrogen and dry solvents. Suggested Equipment: A 2 Uter, four-port graduated glass reactor with central port for introduction of motor propelled stir rod is recommended. The stir rod is preferably multi-tier with angled blades to avoid laminar mixing. The reactor is to be equipped with a heating mantle fitted with a thermocouple and a programmable temperature controller. [Preferably, the mantle has cooling capability as well, in which a fluid filled mantle is used in conjunction with a circulating control unit.] Preferably the reaction volume is not exposed to the thermocouple, but rather the thermocouple is embedded in the heating mantle. Due to the high viscosity of the final product and need for rapid and complete mixing, use of a magnetic stir rod is discouraged. The two free ports are to be equipped with conduits for delivery and removal of nitrogen. The output port is to be connected to an oil trap to prevent backflow of water vapor. Ideally the conduits contain valves to provide for transport of the reaction volume without exposure to air. The last port, the diagnostic port, is to be used for addition and retrieval of reaction volume. The nitrogen atmosphere should be delivered at positive partial pressure to compensate for the external stirring means and periodic opening of the diagnostic port. The partial pressure is indicated by the observation of nitrogen bubbles in the oil trap, and the rate of their creation can be used to set and maintain a reasonable nitrogen flow rate.

Purge the reactor with nitrogen. Add 40.32 grams of PLA diol, obtained from the procedure above and 40.11 grams of Terathane 2000 and 810 ml of toluene using the above setup. Set the stir rate to 100 cycles per minute. The dissolution is accomplished by heating to 115° C., while stirring under nitrogen flow. Upon dissolution the solution volume is to be noted and the temperature is to be raised to 130° C. The nitrogen flow is to be continued until 200 ml of toluene is removed.

Cool the reactor to 15° C. (or room temperature, if the mantle is not equipped with coolant). While stirring, add via the diagnostic port and under nitrogen flow, 30 ml toluene followed by 45.09 grams of IPDI. Stir for 30 minutes. Add drop wise, 6.74 ml dibutyltin dilaurate.

Using the diagnostic port, remove a sample of the solution to measure the % NCO. The % NCO can be measured using dibutylamine back titration. By this method, it is traditional to take at least 3 NCO measurements, or you may do so until a desired standard deviation is obtained.

Raise the temperature of the reactor to 75° C. React the mixture under nitrogen flow for 4 hours at 75° C. Take an NCO. React for another 1 hour, take an NCO. If the NCO at 5 hours is less than 95% of the measurement at 4 hours, continue to react for 1 hour durations until the NCO change is less than 5% between consecutive measurements.

Using the setup of the preparation of the PLA diol, dissolve 12.872 g of butanediol in 230 ml of dry toluene. Dissolution is accomplished by heating to 75° C.

Add the butanediol solution to the reactor. React the mixture under nitrogen flow for 9 hours at 75° C. Take an NCO. React for another 1 hour, take an NCO. If the NCO at 10 hours is less than 95% of the measurement at 9 hours, continue to react for 1 hour durations until the NCO change is less than 5% between consecutive measurements.

During the course of this procedure, toluene may be added to reduce the viscosity of the reactant and improve mixing. Considerable torque can develop during this reaction. When the NCO has stabilized [this should be reproducible from batch to batch, if not water is entering the system], decant the reaction volume to a vacuum chamber. This is easier performed if the reaction volume is still hot. Apply vacuum and remove the toluene, and the resulting solid is to be dissolved in 1000 ml THF. The polymer is then precipitated in 15 L of pentane, filtered, washed with pentane and dried under vacuum at 50° C. n-Pentane can be obtained from Acros and used after re-distillation, and THF (also from Acros) was used as received.

The resulting polyesterurethane has a melt temperature of 132° C. and is soluble in most solvents, for example toluene and acetone.

Example 2: Bioactive

All of the synthesis that is detailed below are to be performed in a hermetically sealed glass reactor equipped with a stir rod and temperature controlled jacket. The head space of the reactor is to be continuously flushed with dry nitrogen unless otherwise specified.

Example 2a: Preparation of a Polyester Diisocyanate

In this example a castor-derived hydroxyl-terminated ricinoleate derivative is used as the diol. One equivalent of polycin D-265 (212 g) is combined with 2 equivalent of toluene diisocyanate (174 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per ½ hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (424 Dalton+2×174 Dalton) yielding approximately 10.9%.

Alternatively, a lower molecular weight diol may be used, such as polycin D-290 where 1 equivalent of polycin D-290 is 193 g and the target % NCO is 84/(386+348)=11.4%.

Alternatively, a higher molecular weight diol may be used, such as polycin D-140 where 1 equivalent of polycin D-140 is 400 g and the target % NCO is 84/(800+348) =7.3%.

All polycin diols are available from Performance Materials (Greensboro, N.C.) and toluene diisocyanate is available from Sigma-Aldrich (Milwaukee, Wis.).

Example 2b: Preparation of a Polyether Diisocyanate

In this example a polyether hydroxyl-terminated copolymer of 75% ethylene oxide and 35% propylene oxide is used as the diol. One equivalent of UCON 75-H-450 (490 g) is combined with 2 equivalent of toluene diisocyanate (174 g) at room temperature (22° C.). The mixture is stirred at 100 revolutions per minute and the temperature monitored.

The mixture will begin to heat up by exothermic reaction and no heat is to be applied to the reactor until the temperature in the reactor ceases to rise. Then the mixture temperature should be increased in 5° C. increments per M hour until the mixture reaches 60° C. The reaction should be continued until the % NCO=10.9%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (980 Dalton+2×174 Dalton) yielding approximately 6.3%. Polyether copolymers of ethylene oxide and propylene oxide diols are available from Dow Chemical (Midland, Mich.).

Example 2c: Preparation of a Polyester Triisocyanate

In this example a castor-derived hydroxyl-terminated ricinoleate derivative is used as the triol. One equivalent of polycin T-400 (141 g) is combined with 2 equivalent of toluene diisocyanate (174 g) at room temperature (22 C). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per M hour until the mixture reaches 60° C. The reaction should be continued until the % NCO=13.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (2×42 Dalton) per product molecule by the total weight of the product molecule (282 Dalton+2×174 Dalton) yielding approximately 13.3%.

The above reaction will yield a viscous product. A less viscous product can be obtained by adding propylene carbonate to the initial mixture. Additions up to 100% by weight of propylene carbonate are useful. Adjustment to the target NCO of the mixture must be performed using standard methods, or the propylene carbonate may be added after reaching the target % NCO. Propylene carbonate is available from Sigma-Aldrich (Milwaukee, Wis.).

Example 2d: Preparation of a Polyether Triisocyanate

In this example a polyether hydroxyl-terminated copolymer of 75% ethylene oxide and 35% propylene oxide is used as the triol. One equivalent of Multranol 9199 (3066 g) is combined with 3 equivalent of toluene diisocyanate (261 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per M6 hour until the mixture reaches 60° C. The reaction should be continued until the % NCO=1.3%. The target % NCO is reached when every hydroxyl group in the mixture is reacted with an NCO group. Ideally, the result is a single diol endcapped with two diisocyanates. This outcome can be enhanced by slow addition of the diol to the diisocyanate. The addition should be in 10 g increments, added when the exotherm from the previous addition has ceased. However, chain extended variations of the above ideal outcome are useful, their primary disadvantage being that the product is slightly higher in viscosity. The ideal % NCO is calculated by dividing the weight of the functional isocyanate groups (3×42 Dalton) per product molecule by the total weight of the product molecule (9199 Dalton+3×174 Dalton) yielding approximately 1.3%. Multranol 9199 is available from Bayer (Pittsburgh, Pa.).

Example 2e: Preparation of a Polyol Triisocyanate from Polyol Diol

Any of the diisocyanates prepared in Examples 2a and 2b can be trimerized by the addition of a low molecular weight triol such as polycin T-400 or trimethylolpropane (TMP). In this example TMP is used, but the method is adaptable to any triol. Complete trimerization of the diisocyanates of Example 2a and 2b will result in viscous products.

To yield a lower viscosity product propylene carbonate can be employed or less triol can be used. In the later case, a mixture of diisocyanate and triisocyanate is obtained. In this example the product of Example 2b is used as the polyether diisocyanate. One equivalent of Example 2b (682 g) is combined with 0.1 equivalent TMP (44.7 g) at room temperature (22° C.). The mixture is stirred at 100 revolutions per minute and the temperature monitored. The mixture will begin to heat up by exothermic reaction and no heat is to be applied to the reactor until the temperature in the reactor ceases to rise. Then the mixture temperature should be increased in 5° C. increments per % hour until the mixture reaches 60° C. The reaction should be continued until the % NCO=5.8%.

The target % NCO is reached when every hydroxyl group in the mixture is reacted with an NCO group. The ideal % NCO is calculated by dividing the weight fraction of the functional isocyanate groups 10%(3×42 Dalton) and 90% (2×42) per product molecule by the total weight fraction of the product molecule (3×1364 Dalton+134 Dalton)+1364 yielding approximately 0.3%+5.5%-5.8%. TMP is available from Sigma-Aldrich (Milwaukee, Wis.).

Example 2f: Preparation of a Modified Boswellia Extract Using the Triisocyanate of Example 2d The hydroxyl number of Boswellia extract will vary depending on extraction method, species of Boswellia extracted, and even variations within species. The goal is to obtain a product with no NCO functionality, so all reaction mixtures should be reacted until the final % NCO=0

In this example the product of Example 2d is used as the polyether triisocyanate mixture. One hundred grams of Example 4 is combined with 1 g of Boswellia extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of Boswellia extract is to be added. By a series of Boswellia addition one calculates the change in % NCO as a function of 1 g additions of Boswellia extract, a linear plot is obtained from which the total amount of Boswellia extract addition necessary to bring the % NCO to zero is obtained. This amount of Boswellia extract is added to the mixture and the mixture is reacted so that % NCO=0 is obtained.

Example 2g: Preparation of a Modified Boswellia Extract Using the Triisocyanate/Diisocyanate of Example 2e The hydroxyl number of Boswellia extract will vary depending on extraction method, species of Boswellia extracted, and even variations within species. The goal is to obtain a product with no NCO functionality, so all reaction mixtures should be reacted until the final % NCO=0.

In this example the product of Example 2e is used as the polyether diisocyanate/triisocyanate mixture. One hundred grams of Example 2e is combined with 1 g of Boswellia extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 then an additional 1 g of Boswellia extract is to be added. By a series of Boswellia addition one calculates the change in % NCO as a function of 1 g additions of Boswellia extract, a linear plot is obtained from which the total amount of Boswellia extract addition necessary to bring the % NCO to zero is obtained. This amount of Boswellia extract is added to the mixture and the mixture is reacted so that % NCO=0 is obtained.

Example 2h: Preparation of a Highly-Branched Modified Boswellia Extract with Absorbable Links Diol and triol can be combined to form a multi-branch polymer. In this instance, the Multranol 9199 triol is chain extended with polycin D-265 diol. The diisocyanate form of Example 2 is useful in chain extending the triisocyanate form of Example 4. We wish to have on average 2 diisocyanates for every 3 triisocyanates, which forms a 5 armed isocyanate.

In this example 0.09 equivalents (292 g) of Example 2d is mixed with 0.04 equivalents (26.6 g) of Example 2b. The triisocyanates of Example 2d and diisocyanates of Example 2b are chain extended with 0.08 equivalents lysine diamine to form a 5 armed isocyanate. One hundred grams of this reaction product is combined with 1 g of Boswellia extract at room temperature (22° C.) under 90% nitrogen and 10% nitric oxide atmosphere. The mixture is stirred at 100 revolutions per minute and the temperature monitored. The mixture will begin to heat up by exothermic reaction. When the temperature ceases to rise, a % NCO reading is taken. If % NCO>0 than an additional 1 g of Boswellia extract is to be added. By a series of Boswellia addition one calculates the change in % NCO as a function of 1 g additions of Boswellia extract, a linear plot is obtained from which the total amount of Boswellia extract addition necessary to bring the % NCO to zero is obtained. This amount of Boswellia extract is added to the mixture and the mixture is reacted so that % NCO=0 is obtained. Lysine diamine is available from Sigma-Aldrich (Milwaukee, Wis.).

Example 3: Surface Texture

A patterned biomaterial of the present disclosure can be given a surface texture by laying down polymer on a textured surface during the print process when the polymer is liquid. Alternatively, the finished biomaterial can be impressed on a heated mold causing the surface of the biomaterial to melt into the mold texture. Textures of particular interest are those with features characterized by multiple size scales, for example, features of approximate size 1 micron, 10 microns and 100 microns. Preferably, the features are superimposed such that the 1 micron features reside on the 10 micron features, and the 10 micron features reside on the 100 micron features.

Figure 1B:
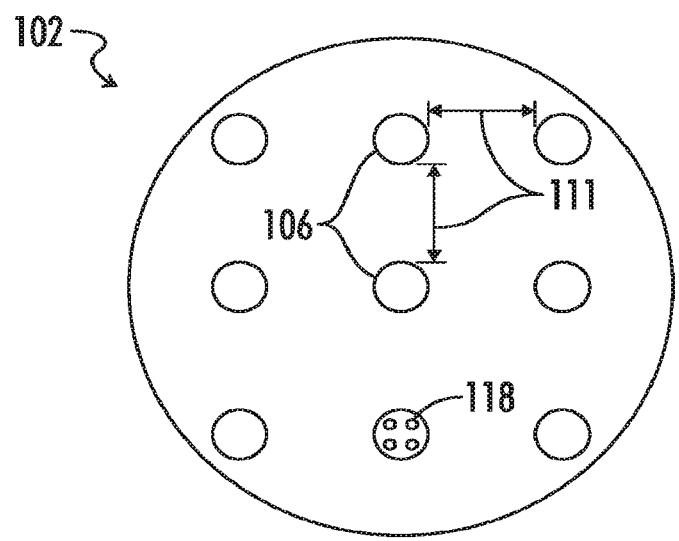

Preferred patterns resemble the surface of rose petals of genus Rosa. Referring to FIG. 1A, depicts a cross sectional view of a a rose pattern mimic 100 is comprised of a large scale pattern 102, the surface of which is approximately a sinusoid or similar undulating surface of amplitude 104 and pitch 105. The amplitude can range from 50 microns to 250 microns. Preferably, the amplitude is 50 microns, more preferably 200 microns, or most preferably 250 microns. The pitch can range from 50 microns to 250 microns. Preferably, the pitch is 50 microns, more preferably 200 microns, or most preferably 250 microns. A medium scale pattern is comprised of cylindrical pillars 106 of diameter 108. Diameter 108 can range from 5 to 50 microns, 10 to 50 microns, 10 to 30 microns or 5 to 20 microns. In some embodiments, the diameter is about 30 microns, more preferably about 20 microns, most preferably about 10 microns. The height 110 of the pillars is approximately 20 to 50 microns. As seen in FIG. 1B represents a top view of large scale structure 102. The pillars 106 are distributed on a square grid 111 of 30 to 100 micron centers. In some embodiments, the centers are about 30 to 80 microns, 40 to 70 microns or about 50 microns.

Figure 1C:
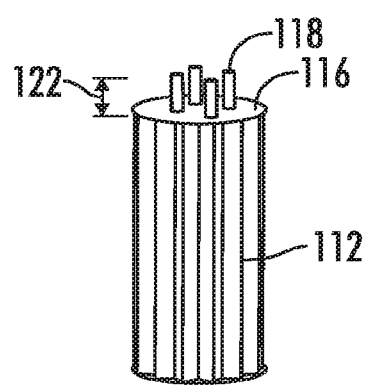
Figure 1D:
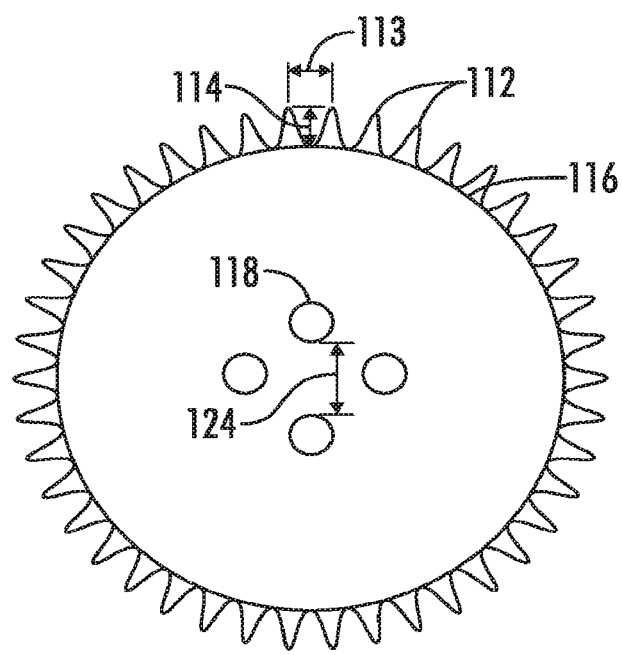

FIG. 1C depictings an expanded view of pillar 106 comprising smaller pillars 118. FIG. 1D depicts an expanded top view of pillar 116 having smaller pillars 118 disposed thereon and ridges 112. Ridges 112 can have a height 114 of 0.5 to 10 microns, 0.5 to 5 microns, about 5 microns, or about 1 micron. The ridges 112 are spaced apart by distance 113 of 1 to 10 microns, or about 5 microns, and approximately parallel along their length. The tops 116 of the pillars 106 may be populated with smaller pillars 118 of diameter 120 0.5 to 5 micron or about 1 micron and height 122 of 0.5 to 1 micron or approximately 1 micron. These smaller pillars 118 are distributed on a square grid 124 of 1 to 10 micron centers, or about 5 micron centers. This rose mimic pattern can in some embodiments be impressed directly on the fibers of the patterned biomaterial or sheets with this pattern can be affixed to portions of the patterned biomaterial.

Example 4: Patterned Biomaterial

Using a print electrospin device containing two print heads, one print head is loaded with a hydrophilic polyesterurethane and the other print head is loaded with a hydrophobic polylactic acid polymer. The print heads are heated such that the polymers are in a liquid state.

Figure 2:
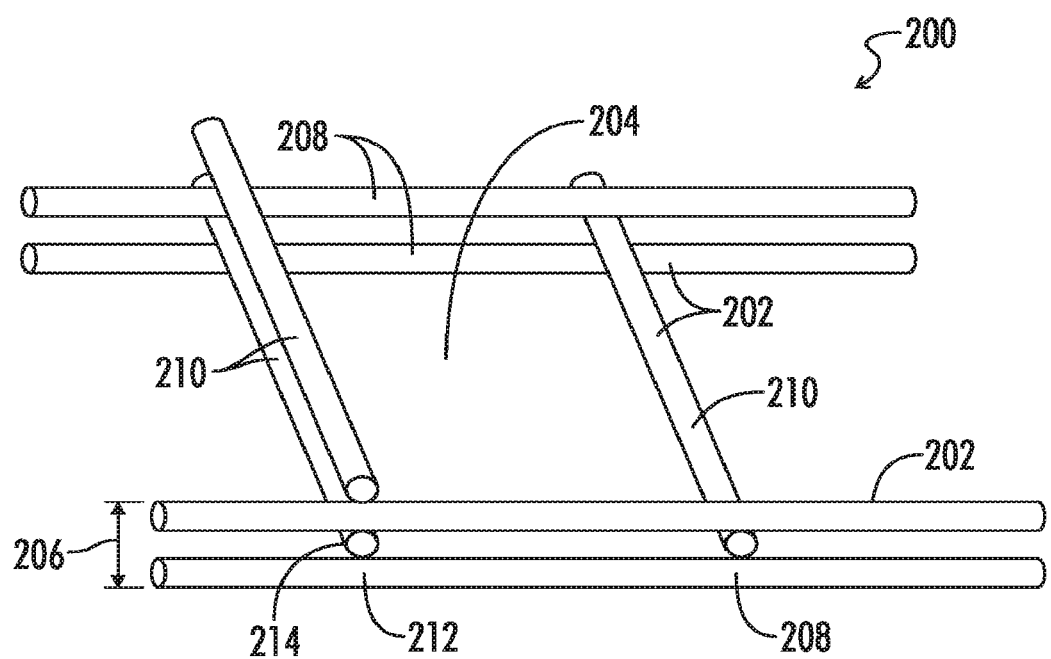
FIG. 2 depicts an exemplary square mesh prepared using an electrospin device and computer aided design

Referring to FIG. 2, the electrospin device is loaded with a computer aided design to form a square mesh 200 design. The square mesh is comprised of fibers 202 arranged in a square pattern where the voids 204 provide an open porous structure suitable for seeding or ingrowth of cells. The patterned biomaterial is comprised of fibers 202 laid down on first and second orthogonal axes to form alternating layers 208 and 210. In one embodiment, the fibers forming layers 208 are hydrophobic and the fibers forming layers 210 are hydrophilic. The height 206 is determined by number of fibers 202 layered or stacked atop one another. The hydrophobic fibers may be a hydrophobic polymer, including but not limited to polypropylene, polycaprolactone, and polylactic acid. Hydrophilic fibers may be hydrophilic polymers, including but not limited to polyether urethanes, polyester urethanes, or polyhyaluronic acid. The fibers are, in some embodiments, nanofibers ranging from about 100 nm to about 5 microns, or about 100 nm to about 1 micron, or about 100 nm to about 500 nm.

In another embodiment, the fibers that form layers 208 are alternately hydrophilic and hydrophobic. In this embodiment, the fibers forming layers 210 are alternately hydrophilic and hydrophobic. Consequently, the juxtaposed lines of layer 208, for example line 212, and layer 210, for example line 214, are either both hydrophilic or both hydrophobic, and are stacked in alternating fashion. The resulting patterned biomaterial is useful for promoting neovascularization at a wound repair site. In some embodiments, the voids 204 have a diameter ranging from 25 microns to 5 mm, 25 microns to 1 mm, 25 microns to 500 microns or 50 microns to 200 microns.

Example 5: Patterned Biomaterial

In some embodiments, the patterned biomaterial is maximally flexible. For example, a chain mail design. In this embodiment, two polymers are delivered in solution. A first polymer is dissolved in a first solvent. A second polymer is dissolved in a second solvent. The second polymer is not soluble in the first solvent. The first polymer is not soluble in the second solvent. Using a print electrospin device, where the polymer stream can be interrupted, a matrix of line segments are laid down.

Figure 3A:
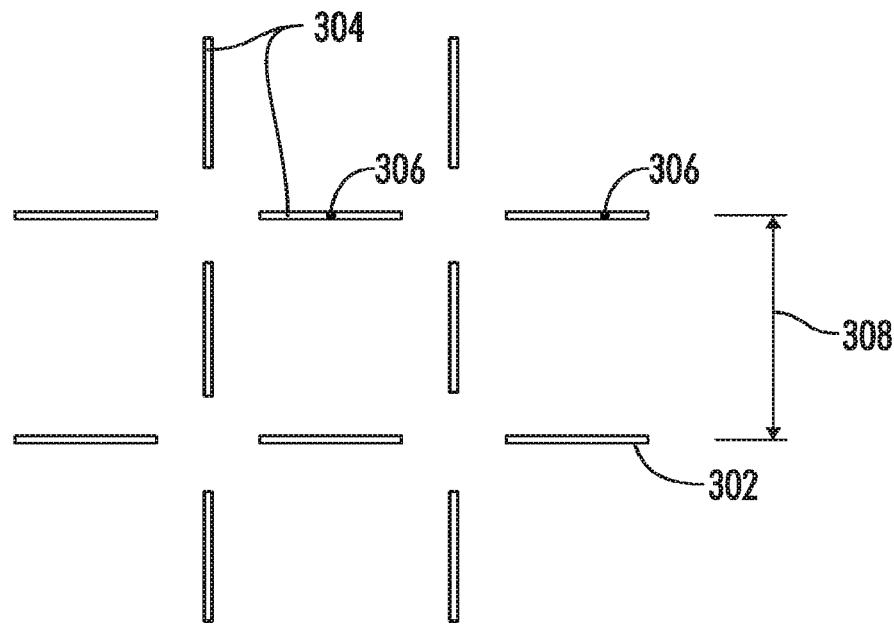
FIG. 3A-3C depicts the construction of a chain mail patterned matrix material.
Figure 3B:
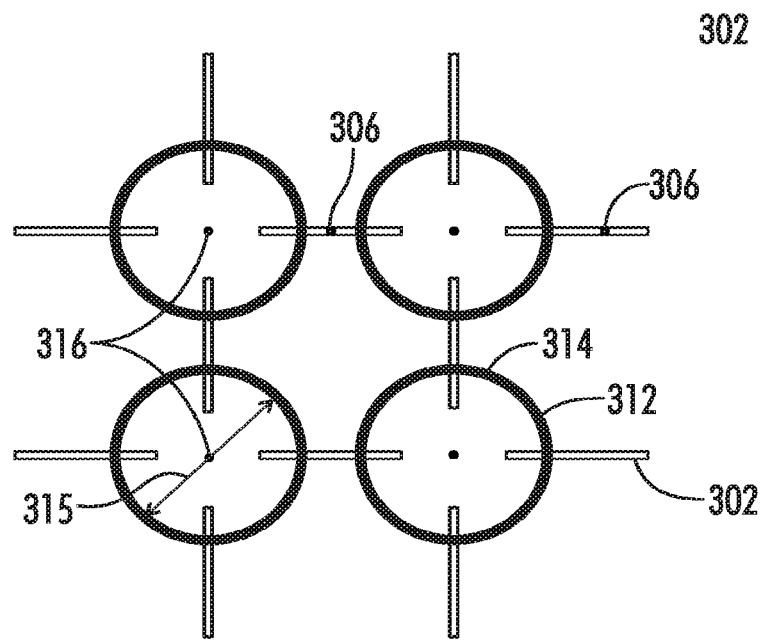
Figure 3C:
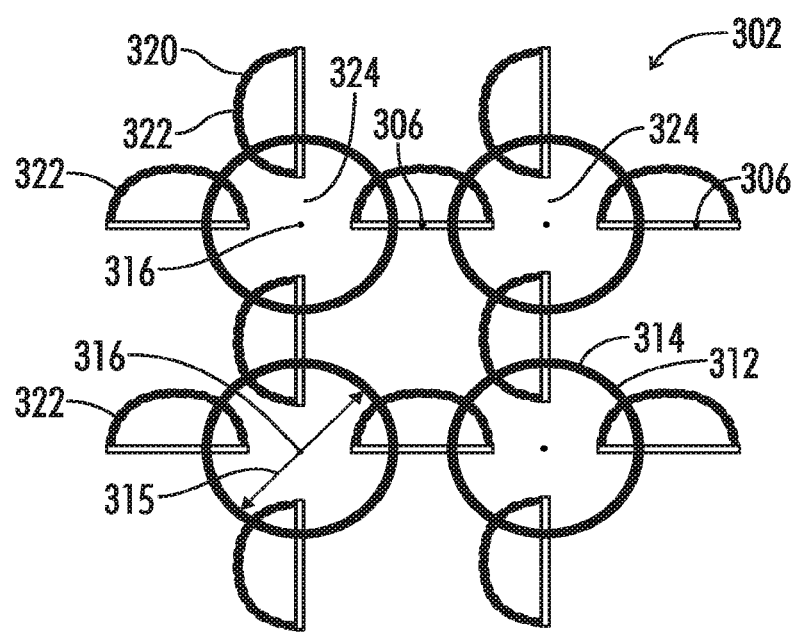

Referring to FIG. 3A-3C, a chain mail patterned biomaterial 300 is constructed by first laying down a square grid 302 of line segments 304, as seen in FIG. 3A. The line segments may have a length of 2000 microns, in some embodiments. The line segments are spaced colinearly on 4000 micron centers 306 and spaced laterally 308 by 4000 microns. The lines 304 comprise a first polymer. After grid 302 has solidified, a second layer 312 comprised of circles 314 is laid down, as depicted in FIG. 3B. Circles 314 may have a diameter of 3000 microns 315 and are centered at intersection points 316. The circles comprise second polymer. The first polymer of 304 is insoluble in the solvent of second polymer 314, such that line segments 304 do not adhere to circles 314. After second layer 312 has solidified third layer 320 is laid down, as depicted in FIG. 3C. Third layer is comprised of the first polymer. Line segments 322 are laid down as depicted, where line segment ends 324 are the only points on line segment 322 in contact with line segments 304. When line segment 322 contacts line segment 304 the solvent in 322 partially dissolves segment 304 such that segments 322 and 304 form a continuous loop. After third layer 320 solidifies, the result is a chain mail structure wherein loops of the first polymer are interlocked with loops of the second polymer, and first polymer loops slidably translate and rotate inside second polymer loops. In some embodiments, the loops have a diameter ranging from 50 microns to 5 mm, 50 microns to 2 mm, 50 microns to 1 mm, 100 microns to 2 mm, 100 microns to 1 mm or 500 microns to 1 mm.

Example 6: Patterned Biomaterial

In some embodiments, a composite sheet and mesh construct is useful in various soft tissue repair applications. In this embodiment, the sheet component is polyesterurethane and the mesh component is polylactic acid, wherein the melt temperature of the polylactic acid is lower than the melt temperature of the polyesterurethane. The polyesterurethane is imprinted with a rose petal pattern designed to prevent migration of the implant and promote endothelial cell motility. In other embodiments, the sheet can be a polylactic acid, a polycaprolactone, polypropylene, polyether urethanes, or polyhyaluronic acid.

Figure 4:
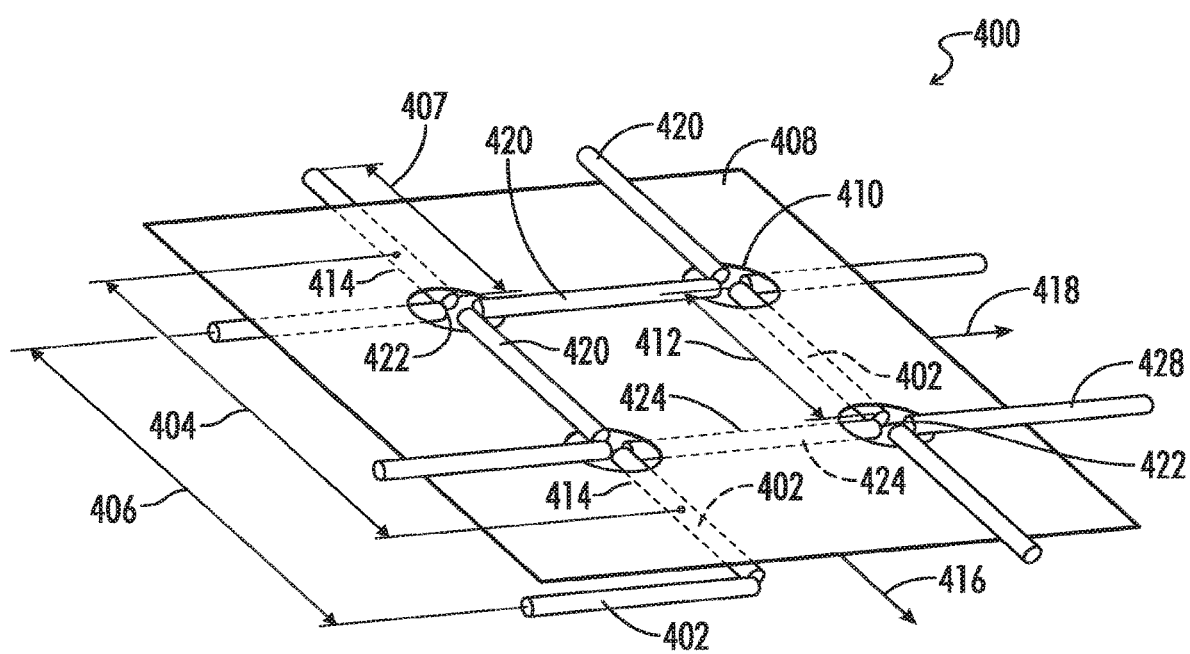
FIG. 4 depicts a composite sheet and mesh patterned biomaterial 400.

Referring to FIG. 4, a composite sheet and mesh patterned biomaterial 400 is depicted. A first layer of lines 402 of polylactic acid is laid down on 8000 micron centers 404 and spaced apart 406 by 8000 microns. Each line 402 is 3500 microns long 407. A sheet of polyesterurethane 408 is comprised of 1000 micron diameter holes 410 spaced 4000 microns apart 412. The sheet 408 is registered with respect to line grid 402 such that the space 414 between line segments 402 is centered between sheet holes 410 in two dimensions 416 and 418. After registration, a second layer of polylactic acid lines 420 is laid down. At each endpoint 422 of each line 424 is started a line 420 that terminates at a second endpoint 426 of an adjacent line 428. The temperature of the polylactic acid is sufficient to melt-bond endpoints 422 and 426 to line 420, such that when solid, polylactic acid lines weave above and below the polyesterurethane sheet. The hydrophobic polylactic acid strands promote fibroblasts through the polyesterurethane sheet whereas the textured surface of the polyesterurethane sheet promotes endothelialization and neovascularization in the plane of the polyesterurethane sheet.

Example 7: Patterned Biomaterial

In some embodiments a three dimensional mesh is desired. A three dimensional mesh can be printed on a two dimensional surface. Square matrices of lines can be stacked without adhesion by laying down a first square matrix of melt polymer, cooling this layer sufficiently such that when a second layer of square matrix is laid down over the first, the second layer solidifies prior to the first layer heating sufficiently to melt. Non-adhering layers stacked in this way can be connected together by running a diagonal line of polymer melt such that the diagonal line melts into the vertices of the stacked square matrices.

Figure 5:
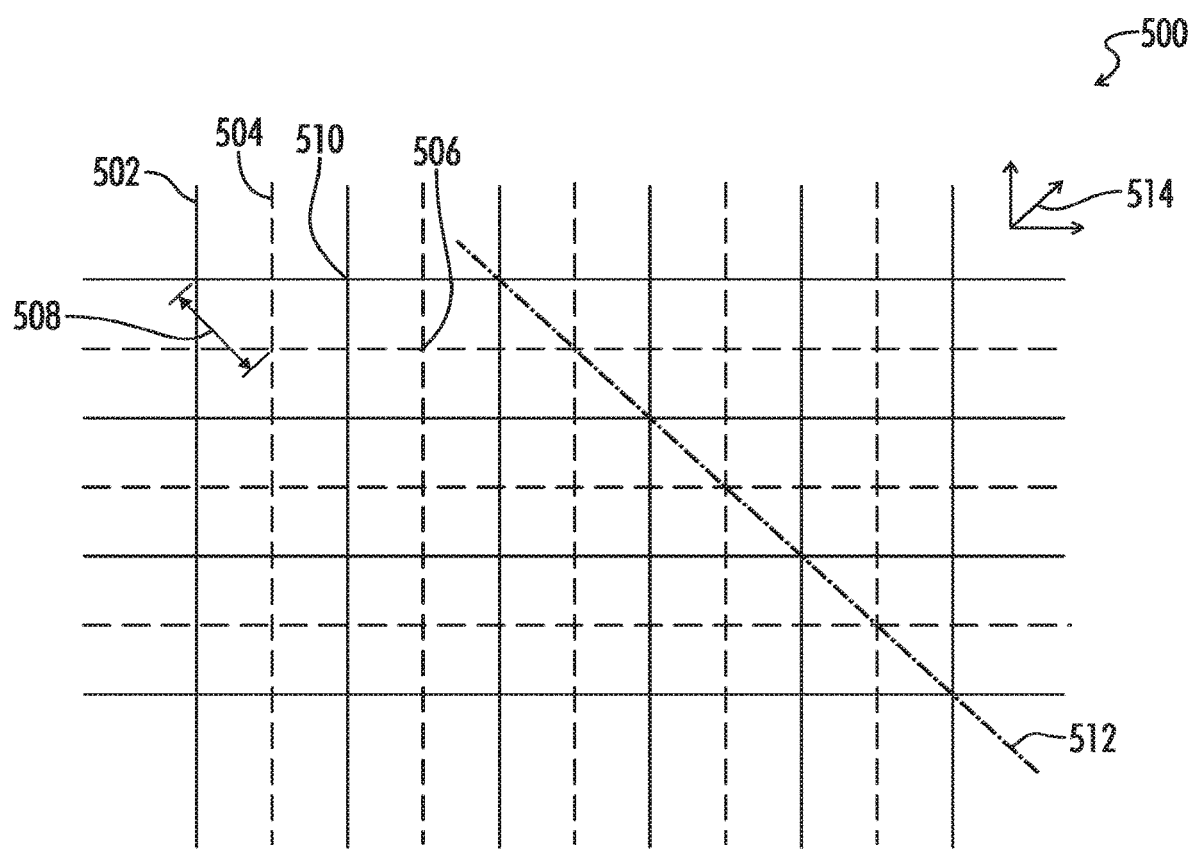
FIG. 5 depicts a three dimensional mesh 500 is depicted.

Referring to FIG. 5, a three dimensional mesh 500 is depicted. First square matrix 502 is laid down and solidified and cooled to 20 centigrade below the melting point. Then a second square matrix 504 is laid down such that the intersection points 506 of matrix 504 are diagonally offset distance 508 from intersection points 510 of matrix 502. An arbitrary number of matrices of type 502 can be laid down without adherence between them. In a final step, polymer is laid down in diagonal lines 512. The polymer bonds at the intersection points 506 and 510 joining matrices 504 and 502, respectively. The patterned biomaterial can be expanded in a third dimension 514 by suspending the biomaterial from diagonal lines 512 and heating sufficient to relax the polymers without melting them.

Figure 6:
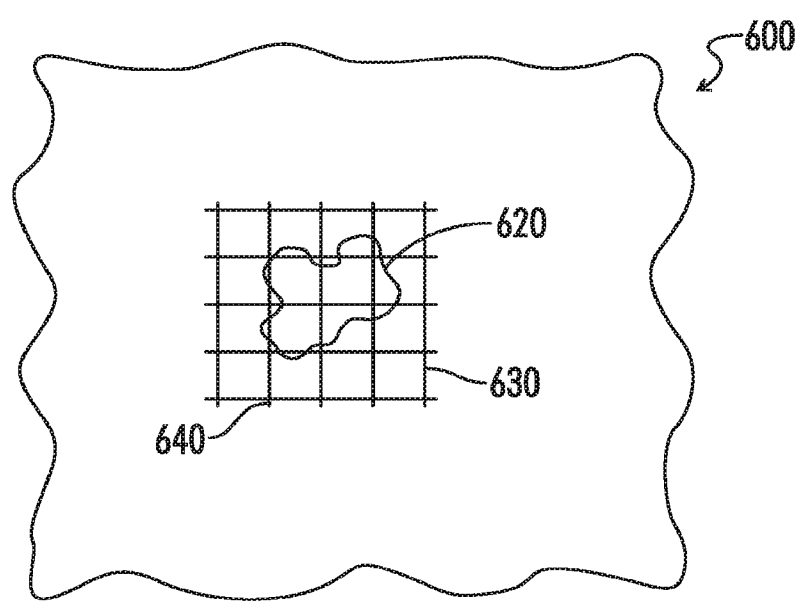
FIG. 6 depicts an exemplary mesh device as used with human tissue having a defect to be repaired.

Referring now to FIG. 6, an exemplary mesh device is depicted. A human tissue with defect and an implant modification 600 comprises a human tissue 610. 610 can be bone, muscle, or any structure in the body that can be repaired endogenously by cellular infiltration. 610 contains a defect 620. Microtextured haptotaxic implant is in this instance a mesh 630, the filaments 640 of the mesh are selected to promote functional repair of the defect.

Figure 7:
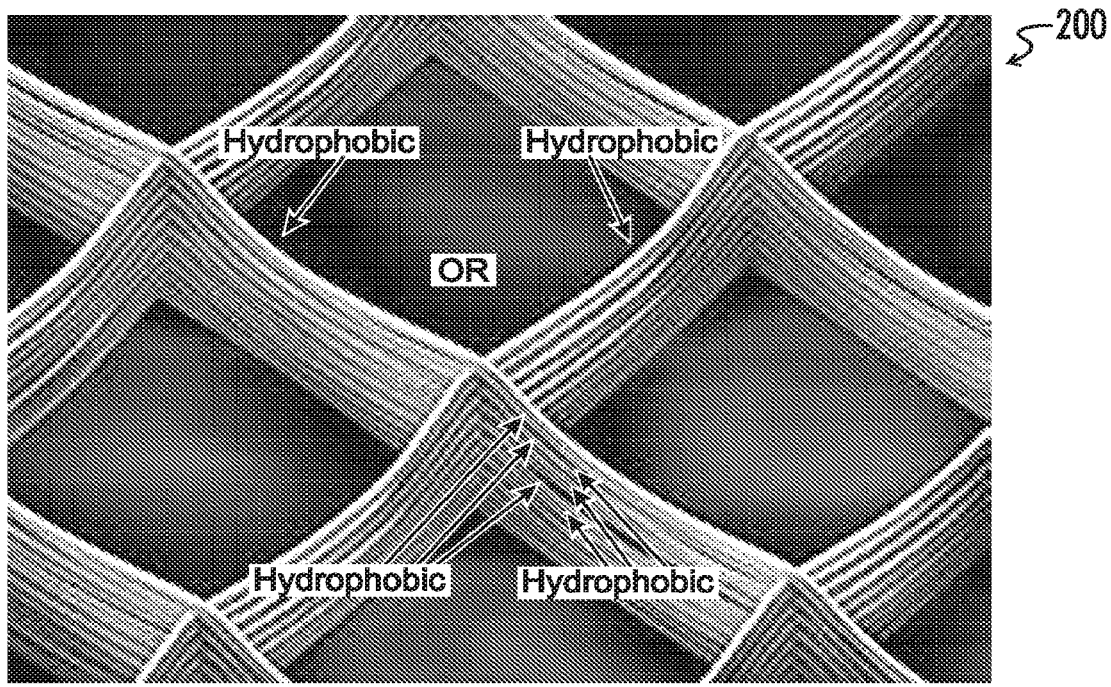
FIG. 7 is an image of a mesh according to the present disclosure having alternating hydrophobic and hydrophilic fibers.

FIG. 7 is an image of a mesh 200 according to the present disclosure having alternating hydrophobic and hydrophilic fibers. In some embodiments, the fibers alternate as they are stacked, while in other embodiments, the fibers alternate adjacent to one another.

Figure 8:
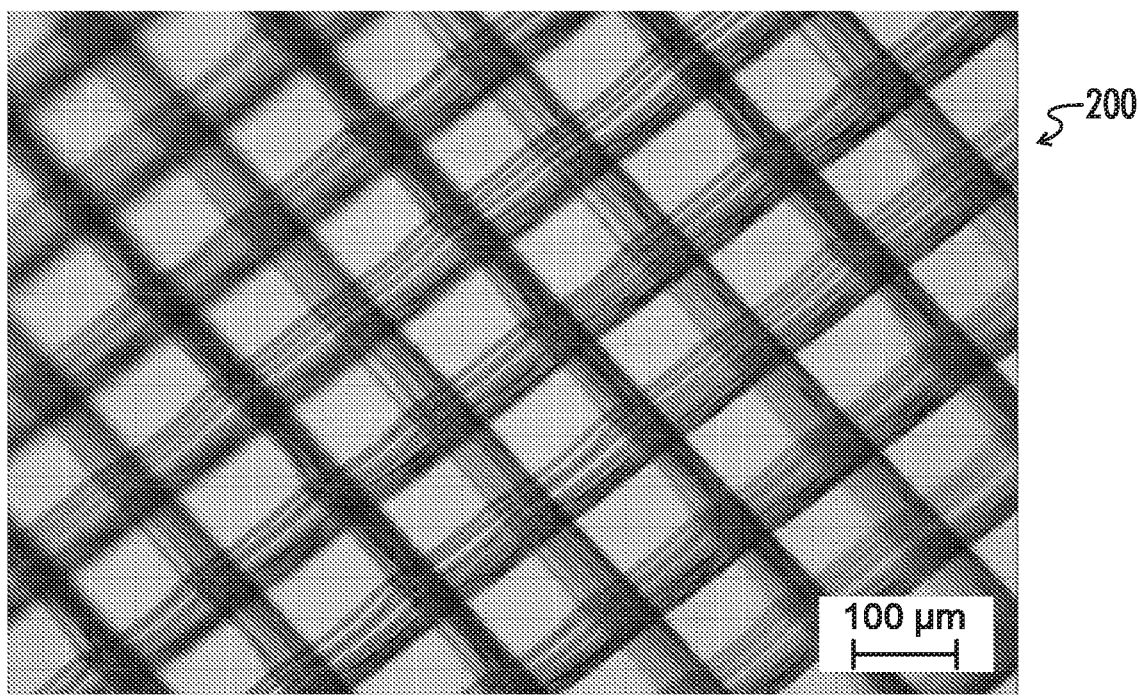
FIG. 8 is another image of an embodiment of a mesh according to the present disclosure.

FIG. 8 is another image of an embodiment of a mesh 200 according to the present disclosure.

Figure 9:
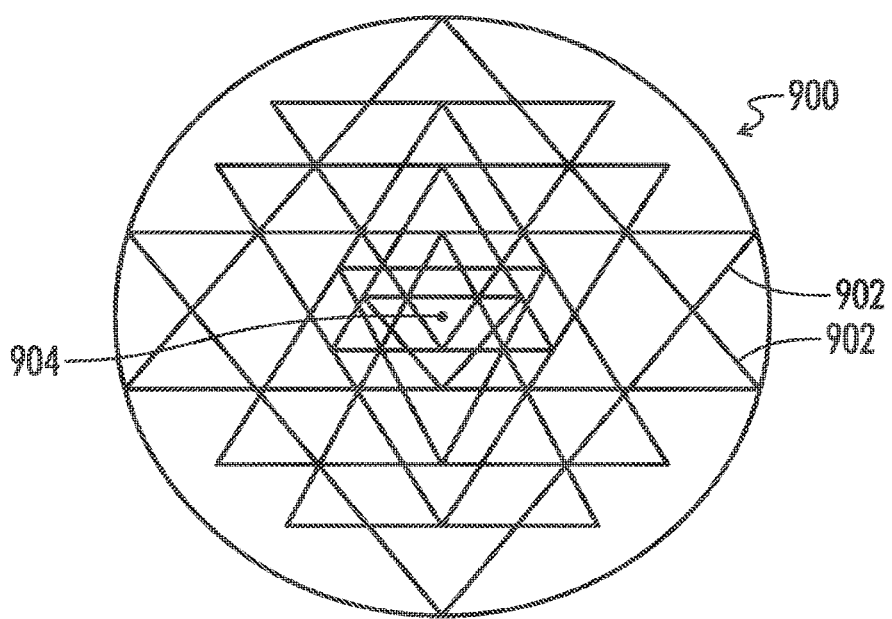
FIG. 9 is a further design of a device, in which fibers are arranged in a series of stacked triangles. The polymer fibers can alternate between hydrophilic and hydrophobic fibers.

FIG. 9 is further matrix pattern 900, in which fibers are arranged in a series of stacked triangles 902, which are centered about a point 904. The triangles compares polymer nanofibers and can alternate between hydrophilic and hydrophobic fibers.

Figure 10:
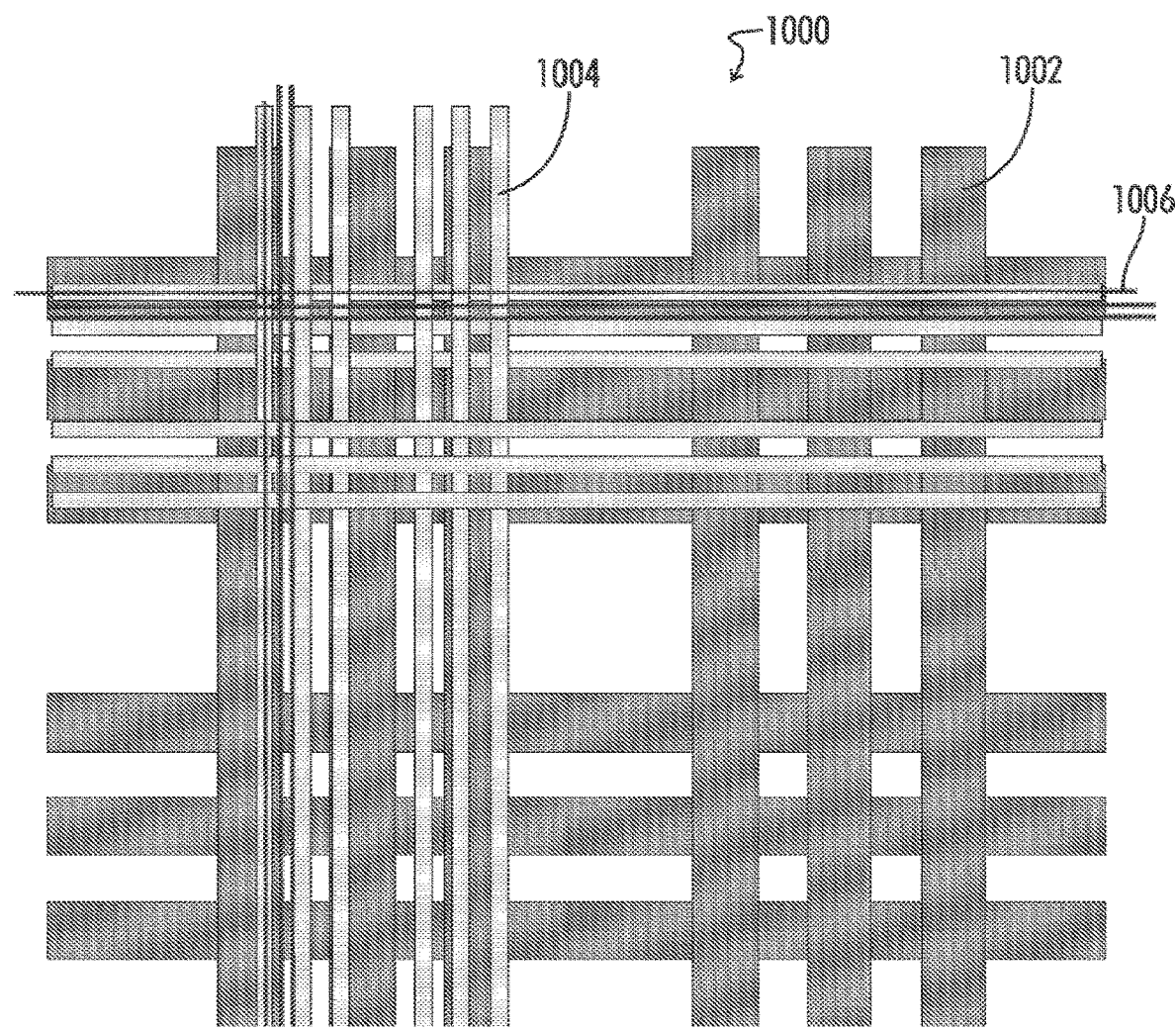
FIG. 10 depicts an alternative rose petal mimic having a hierarchical grid pattern with created by layers of varying width.

FIG. 10 depicts a matrix having an alternative rose petal mimic 1000 having fibers disposed in a hierarchical grid pattern. The grid is formed from a macro layers of 50 microns to 1 mm (1002), meso layers of 1 micron to 50 micron (1004) and fine layers of less than 1 micron (1006). In some embodiments, the macro scale ranges from 50 microns to 500 microns, or 100 microns to 500 microns. In some embodiments, the meso scale ranges from 10 microns to 30 microns or 5 microns to 25 microns. In some embodiments, the fine scale ranges from 0.1 micron to 1 micron, 1.1 micron to 0.75 micron or 0.25 micron to 0.75 micron. The surface energy of the matrix thus is varied on at least three spatial scales comprising 1) a macro scale ranging from 50 micron to 1 mm obtained by forming layers of polymers of different surface energy, 2) a meso scale ranging from 1 micron to 50 micron obtained by placing a surface pattern on the polymers, and 3) a fine-scale of less than 1 micron obtained by variation of molecular structure.

What is claimed is:

1. A three-dimensional matrix for tissue regeneration comprising at least three successive layers of at least two biocompatible polymers that are solid at temperature below 36° C., the layers arranged to form walls with open voids therebetween, the voids suitable for seeding or ingrowth of cells, the layers comprising a first polymer and a second polymer, the first or second polymer comprising polyester urethane, polyether urethane or a combination thereof, and wherein the first and second polymers are disposed in an alternating pattern along at least one axis of the matrix, wherein the first polymer is hydrophobic and/or lipophilic and the second polymer is hydrophilic; and wherein the matrix has a surface energy, the surface energy being varied on at least three spatial scales comprising 1) a macro scale ranging from 50 micron to 1 mm obtained by forming layers of polymers of different surface energy, 2) a meso scale ranging from 1 micron to 50 micron obtained by placing a surface pattern on the polymers, and 3) a fine-scale of less than 1 micron obtained by variation of molecular structure.

2. The matrix of claim 1, wherein the first and second polymers are nanofibers.

3. The matrix of claim 1, wherein the walls intersect at junctions along the first axes and second axes, the first axes being parallel first axes, and wherein the walls comprise alternating layers of the first and second polymers along second axes are perpendicular to the first axes.

4. The matrix of claim 1, wherein the matrix is formed on an implantable substrate.

5. The matrix of claim 4, wherein the implantable substrate and the matrix are bioabsorbable, and wherein the implantable substrate bioabsorbs more rapidly than the matrix.

6. The matrix of claim 1, wherein the three-dimensional matrix further comprises a bioactive agent.

7. The matrix of claim 2, wherein the nanofibers include a diameter from 100 nm to 5 microns.

8. The matrix of claim 2, wherein the nanofibers include a diameter from 100 nm to 500 microns.

9. The matrix of claim 1, wherein the at least first polymer comprises polypropylene, polycaprolactone, polylactic acid, or combinations thereof.

10. The matrix of claim 1, wherein the at least second polymer comprises polyether urethane, polyester urethane, polyhyaluronic acid, or combinations thereof.

11. The matrix of claim 10, wherein the at least second polymer comprises polyether urethane, polyester urethane, polyhyaluronic acid, or combinations thereof.

12. A three-dimensional matrix for tissue regeneration comprising:

a substrate having at least three successive layers of at least two biocompatible polymers that are solid at temperature below 36° C., the layers arranged to form walls with open voids therebetween, the voids suitable for seeding or ingrowth of cells, the layers comprising a first polymer and a second polymer, comprising polyester urethane, polyether urethane or a combination thereof, and wherein the first and second polymers are disposed in an alternating pattern along at least one axis of the matrix, wherein the first polymer is hydrophobic and/or lipophilic and the second polymer is hydrophilic;

an implantable layer wherein the substrate is disposed on the implantable layer; and wherein the matrix has a surface energy, the surface energy being varied on at least three spatial scales comprising 1) a macro scale ranging from 50 micron to 1 mm obtained by forming layers of polymers of different surface energy, 2) a meso scale ranging from 1 micron to 50 micron obtained by placing a surface pattern on the polymers, and 3) a fine-scale of less than 1 micron obtained by variation of molecular structure.

13. The matrix of claim 12, wherein the first and second polymers are nanofibers.

14. The matrix of claim 12, wherein the walls intersect at junctions along parallel first axes, and wherein the walls comprise alternating layers of the first and second polymers along second axes perpendicular to the first axes.

15. The matrix of claim 12, wherein the substrate and the implantable layer are bioabsorbable, and wherein the implantable layer bioabsorbs more rapidly than the substrate.

16. The matrix of claim 12, wherein the three-dimensional matrix further comprises a bioactive agent.

17. The matrix of claim 13, wherein the nanofibers include a diameter from 100 nm to 5 microns.

18. The matrix of claim 13, wherein the nanofibers include a diameter from 100 nm to 500 microns.

19. The matrix of claim 12, wherein the at least first polymer comprises polypropylene, polycaprolactone, polylactic acid, or combinations thereof.

20. The matrix of claim 12, wherein the at least second polymer comprises polyether urethane, polyester urethane, polyhyaluronic acid, or combinations thereof.

* * * * *